(12) United States Patent
de Beaubien et al.

(10) Patent No.: US 12,239,538 B2
(45) Date of Patent: Mar. 4, 2025

(54) SYSTEM AND METHOD FOR TREATMENT AND PREVENTION OF PERIPROSTHETIC JOINT INFECTIONS

(71) Applicant: Osteal Therapeutics, Inc., San Clemente, CA (US)

(72) Inventors: Brian de Beaubien, Fenton, MI (US); Jude Paganelli, Coronado, CA (US); Daniel Pflaster, Charlotte, VT (US); Daivon Deans, San Diego, CA (US); Ryan Watson, Boulder, CO (US); Brian Bowman, Carlsbad, CA (US)

(73) Assignee: Osteal Therapeutics, Inc., Dallas, TX (US)

( * ) Notice: Subject to any disclaimer, the term of this patent is extended or adjusted under 35 U.S.C. 154(b) by 619 days.

(21) Appl. No.: 17/401,843

(22) Filed: Aug. 13, 2021

(65) Prior Publication Data

US 2022/0047392 A1 Feb. 17, 2022

Related U.S. Application Data

(60) Provisional application No. 63/065,413, filed on Aug. 13, 2020.

(51) Int. Cl.
*A61F 2/30* (2006.01)
*A61F 2/36* (2006.01)
(Continued)

(52) U.S. Cl.
CPC ............ *A61F 2/30724* (2013.01); *A61F 2/36* (2013.01); *A61F 2/389* (2013.01); *A61F 2/4014* (2013.01);
(Continued)

(58) Field of Classification Search
CPC ............................................. A61F 2002/3613
See application file for complete search history.

(56) References Cited

U.S. PATENT DOCUMENTS 3,648,294 A 3/1972 Shahrestani
4,274,163 A 6/1981 Malcom et al.
(Continued)

FOREIGN PATENT DOCUMENTS

CN 104168857 A 11/2014
DE 3704089 A1 8/1988
(Continued)

OTHER PUBLICATIONS

Thabe, H. et al. (2007). "Two-stage Reimplantation with an Application Spacer and Combined with Delivery of Antibiotics in the Management of Prosthetic Joint Infection" Oper. Orthop Traumatol, 1:78-100. [German language and English language].
(Continued)

*Primary Examiner* — Megan Y Wolf
(74) *Attorney, Agent, or Firm* — Mintz Levin Cohn Ferris Glovsky and Popeo, P.C.

(57) ABSTRACT

Provided herein are rapid and effective local infection therapy methods, systems, and devices that significantly reduce the mortality, morbidity, and the cost of care in rare musculoskeletal infections. Continuous delivery of antibiotic therapy locally, at the infection site, reduces edema and provides antibiotic irrigation, significantly improving outcomes while reducing the need for systemic antibiotics.

14 Claims, 26 Drawing Sheets

(51) Int. Cl.
  *A61F 2/38* (2006.01)
  *A61F 2/40* (2006.01)
  *A61M 1/00* (2006.01)

(52) U.S. Cl.
  CPC ....... *A61M 1/90* (2021.05); *A61F 2002/3006* (2013.01); *A61F 2002/30672* (2013.01); *A61F 2002/30677* (2013.01)

(56) References Cited

U.S. PATENT DOCUMENTS

| | | |
|---|---|---|
| 4,399,814 A | 8/1983 | Pratt, Jr. et al. |
| 4,488,549 A | 12/1984 | Lee et al. |
| 4,653,487 A | 3/1987 | Maale |
| 4,711,233 A | 12/1987 | Brown |
| 4,888,024 A | 12/1989 | Powlan |
| 4,892,550 A | 1/1990 | Huebsch |
| 5,116,377 A | 5/1992 | Skripitz et al. |
| 5,133,767 A | 7/1992 | Frey et al. |
| 5,133,771 A | 7/1992 | Duncan et al. |
| 5,133,772 A | 7/1992 | Hack et al. |
| 5,156,606 A | 10/1992 | Chin |
| 5,290,291 A | 3/1994 | Linden |
| 5,340,362 A | 8/1994 | Carbone |
| 5,370,698 A | 12/1994 | Heimke et al. |
| 5,376,123 A | 12/1994 | Klaue et al. |
| 5,433,718 A | 7/1995 | Brinker |
| 5,501,687 A | 3/1996 | Willert et al. |
| 5,514,137 A | 5/1996 | Coutts |
| 5,549,702 A | 8/1996 | Ries et al. |
| 5,554,111 A | 9/1996 | Morrey et al. |
| 5,562,736 A | 10/1996 | Ray et al. |
| 5,571,204 A | 11/1996 | Nies |
| 5,618,286 A | 4/1997 | Brinker |
| 5,681,289 A | 10/1997 | Wilcox et al. |
| 5,683,472 A | 11/1997 | O'Neil et al. |
| 5,693,099 A | 12/1997 | Harle |
| 5,702,446 A | 12/1997 | Schenck et al. |
| 5,725,596 A | 3/1998 | Burke |
| 5,741,265 A | 4/1998 | Chan |
| 5,755,811 A | 5/1998 | Tanamal et al. |
| 5,827,289 A | 10/1998 | Reiley et al. |
| 5,871,484 A | 2/1999 | Spievack et al. |
| 5,916,269 A * | 6/1999 | Serbousek ............ A61F 2/3859 623/22.24 |
| 5,954,771 A | 9/1999 | Richelsoph et al. |
| 5,980,573 A | 11/1999 | Shaffner |
| 6,066,154 A | 5/2000 | Reiley et al. |
| 6,106,495 A | 8/2000 | Scott |
| 6,113,639 A | 9/2000 | Ray et al. |
| 6,132,674 A | 10/2000 | Compton et al. |
| 6,155,812 A | 12/2000 | Smith et al. |
| 6,217,619 B1 | 4/2001 | Keller |
| 6,235,043 B1 | 5/2001 | Reiley et al. |
| 6,248,110 B1 | 6/2001 | Reiley et al. |
| 6,336,941 B1 | 1/2002 | Subba Rao et al. |
| 6,361,731 B1 | 3/2002 | Smith et al. |
| 6,361,780 B1 | 3/2002 | Ley et al. |
| 6,423,083 B2 | 7/2002 | Reiley et al. |
| 6,447,514 B1 | 9/2002 | Stalcup et al. |
| 6,544,472 B1 | 4/2003 | Compton et al. |
| 6,589,281 B2 | 7/2003 | Hyde, Jr. |
| 6,679,890 B2 | 1/2004 | Margulies et al. |
| 6,692,529 B2 | 2/2004 | Shah |
| 6,740,090 B1 | 5/2004 | Cragg et al. |
| 6,740,120 B1 | 5/2004 | Grimes |
| 6,783,515 B1 | 8/2004 | Miller et al. |
| 6,899,716 B2 | 5/2005 | Cragg |
| 6,921,403 B2 | 7/2005 | Cragg et al. |
| 6,942,475 B2 | 9/2005 | Ensign et al. |
| 6,942,702 B2 | 9/2005 | Mitsugi et al. |
| 6,969,404 B2 | 11/2005 | Ferree |
| 6,979,336 B2 | 12/2005 | Durniak |
| 6,981,981 B2 | 1/2006 | Reiley et al. |
| 6,989,033 B1 | 1/2006 | Schmidt |
| 7,048,743 B2 | 5/2006 | Miller et al. |
| 7,112,205 B2 | 9/2006 | Carrison |
| 7,141,053 B2 | 11/2006 | Rosa et al. |
| 7,141,067 B2 | 11/2006 | Jones et al. |
| 7,211,113 B2 | 5/2007 | Zelener et al. |
| 7,217,260 B2 | 5/2007 | Molander et al. |
| 7,250,055 B1 | 7/2007 | Vanderwalle |
| 7,255,713 B2 | 8/2007 | Malek |
| 7,300,282 B2 | 11/2007 | Sapian |
| 7,306,629 B2 | 12/2007 | Saladino et al. |
| 7,427,296 B2 | 9/2008 | Evans |
| 7,429,346 B2 | 9/2008 | Ensign et al. |
| 7,534,240 B1 | 5/2009 | Johnson |
| 7,572,293 B2 | 8/2009 | Rhodes et al. |
| 7,601,157 B2 | 10/2009 | Boyd et al. |
| 7,601,176 B2 | 10/2009 | Soffiati et al. |
| 7,641,698 B1 | 1/2010 | Gibbs et al. |
| 7,771,428 B2 | 8/2010 | Siravo et al. |
| 7,842,095 B2 | 11/2010 | Klein |
| 7,862,619 B2 | 1/2011 | Clark |
| 7,914,585 B2 | 3/2011 | Keller |
| 8,038,682 B2 | 10/2011 | McGill et al. |
| 8,097,039 B2 | 1/2012 | Evans |
| 8,135,466 B2 | 3/2012 | Fuller et al. |
| 8,366,782 B2 | 2/2013 | Wright |
| 8,388,881 B2 | 3/2013 | Giori |
| 8,454,706 B2 | 6/2013 | de Beaubien |
| 8,475,505 B2 | 7/2013 | Nebosky et al. |
| 8,496,711 B2 | 7/2013 | Anapliotis et al. |
| 8,500,819 B2 | 8/2013 | Meridew et al. |
| 8,529,532 B2 | 9/2013 | Pinto et al. |
| 8,579,985 B2 | 11/2013 | Podolsky et al. |
| 8,608,802 B2 | 12/2013 | Bagga et al. |
| 8,652,216 B2 | 2/2014 | Chen et al. |
| 8,673,018 B2 | 3/2014 | Walls |
| 8,685,432 B2 | 4/2014 | Evans et al. |
| 8,721,520 B2 | 5/2014 | Caira et al. |
| 8,974,538 B2 | 3/2015 | Teeny et al. |
| 9,173,742 B2 | 11/2015 | Faccioli et al. |
| RE46,283 E | 1/2017 | de Beaubien |
| 9,707,008 B2 | 7/2017 | Krebs et al. |
| 9,795,486 B2 | 10/2017 | Faccioli et al. |
| RE46,669 E | 1/2018 | de Beaubien |
| 9,925,363 B2 | 3/2018 | Magagnoli |
| 10,265,182 B2 | 4/2019 | Foran |
| 10,433,965 B2 | 10/2019 | de Beaubien et al. |
| 10,624,794 B2 | 4/2020 | Sides et al. |
| 2001/0051831 A1 | 12/2001 | Subba Rao et al. |
| 2002/0143402 A1 | 10/2002 | Steinberg |
| 2002/0169507 A1 | 11/2002 | Malone |
| 2003/0060891 A1 | 3/2003 | Shah |
| 2003/0097184 A1 | 5/2003 | Mitsugi et al. |
| 2003/0187513 A1 | 10/2003 | Durniak |
| 2004/0036189 A1 | 2/2004 | Ensign et al. |
| 2004/0111162 A1 | 6/2004 | Southworth |
| 2004/0193268 A1 | 9/2004 | Hazebrouck |
| 2004/0193281 A1 | 9/2004 | Grimes |
| 2004/0225360 A1 | 11/2004 | Malone |
| 2005/0004680 A1 | 1/2005 | Saladino et al. |
| 2005/0021084 A1 | 1/2005 | Lu et al. |
| 2005/0107794 A1 | 5/2005 | Hazebrouck |
| 2005/0187555 A1 | 8/2005 | Biedermann et al. |
| 2005/0277936 A1 | 12/2005 | Siravo et al. |
| 2006/0004431 A1 | 1/2006 | Fuller et al. |
| 2006/0014120 A1 | 1/2006 | Sapian |
| 2006/0030945 A1 | 2/2006 | Wright |
| 2006/0093646 A1 | 5/2006 | Cima et al. |
| 2006/0121083 A1 | 6/2006 | Mor |
| 2007/0005142 A1 | 1/2007 | Rhodes et al. |
| 2007/0016163 A1 | 1/2007 | Santini et al. |
| 2007/0088442 A1 | 4/2007 | Cima et al. |
| 2007/0110804 A1 | 5/2007 | Royer |
| 2007/0123835 A1 | 5/2007 | Molander et al. |
| 2007/0179609 A1 | 8/2007 | Goble et al. |
| 2009/0069899 A1 | 3/2009 | Klein |
| 2009/0130167 A1 | 5/2009 | Shelton et al. |
| 2010/0042167 A1 | 2/2010 | Nebosky et al. |
| 2010/0042213 A1 | 2/2010 | Nebosky et al. |

(56) References Cited

U.S. PATENT DOCUMENTS

| | | | |
|---|---|---|---|
| 2010/0042214 A1* | 2/2010 | Nebosky | A61F 2/36 604/93.01 |
| 2010/0042215 A1 | 2/2010 | Stalcup et al. | |
| 2010/0114324 A1 | 5/2010 | Gibbs et al. | |
| 2010/0217401 A1 | 8/2010 | de Beaubien | |
| 2010/0292803 A1 | 11/2010 | Giori | |
| 2011/0015754 A1* | 1/2011 | Leonard | A61F 2/3609 623/22.42 |
| 2011/0208315 A1 | 8/2011 | Anapliotis et al. | |
| 2011/0218644 A1 | 9/2011 | Meridew et al. | |
| 2011/0236501 A1 | 9/2011 | Guelcher et al. | |
| 2012/0109303 A1 | 5/2012 | Capote | |
| 2013/0041472 A1 | 2/2013 | Rabiner et al. | |
| 2013/0158595 A1 | 6/2013 | Mavani et al. | |
| 2013/0209522 A1 | 8/2013 | Brooks et al. | |
| 2013/0211334 A1 | 8/2013 | de Beaubien | |
| 2013/0211369 A1 | 8/2013 | de Beaubien | |
| 2013/0218100 A1 | 8/2013 | Armbruster et al. | |
| 2013/0237908 A1 | 9/2013 | Clark | |
| 2013/0289621 A1 | 10/2013 | Fulmer et al. | |
| 2014/0194810 A1 | 7/2014 | Barsoum et al. | |
| 2015/0038941 A1 | 2/2015 | Nebosky et al. | |
| 2016/0199190 A1 | 7/2016 | Sharifi-Mehr et al. | |
| 2016/0367371 A1* | 12/2016 | de Beaubien | A61F 2/38 |
| 2017/0354507 A1* | 12/2017 | Foran | A61F 2/3859 |
| 2019/0290833 A1 | 9/2019 | Vogt et al. | |
| 2019/0290834 A1 | 9/2019 | Vogt et al. | |
| 2020/0038191 A1 | 2/2020 | de Beaubien et al. | |
| 2020/0222196 A1 | 7/2020 | Vogt et al. | |
| 2020/0323695 A1 | 10/2020 | Sides et al. | |
| 2020/0330660 A1 | 10/2020 | Patel et al. | |
| 2020/0330661 A1 | 10/2020 | Canner et al. | |
| 2020/0360578 A1 | 11/2020 | Loske et al. | |
| 2021/0069409 A1 | 3/2021 | Castleberry et al. | |
| 2021/0085467 A1 | 3/2021 | Dietz et al. | |
| 2021/0386942 A1 | 12/2021 | Brown et al. | |
| 2022/0249238 A1 | 8/2022 | Link et al. | |

FOREIGN PATENT DOCUMENTS

| | | |
|---|---|---|
| DE | 19722359 A1 | 12/1998 |
| DE | 19722389 A1 | 12/1998 |
| DE | 102010052914 A1 | 5/2012 |
| EP | 0692226 A1 | 1/1996 |
| EP | 2326287 B1 | 5/2016 |
| IT | VI 20000025 U1 | 10/2001 |
| JP | 2005-028129 A | 2/2005 |
| JP | 2012-500056 A | 1/2012 |
| JP | 2014-176714 A | 9/2014 |
| KR | 101377900 B1 | 3/2014 |
| NZ | 279442 A | 2/1998 |
| WO | WO-03/037166 A2 | 5/2003 |
| WO | WO-2005/006938 A2 | 1/2005 |
| WO | WO-2007/047420 A2 | 4/2007 |
| WO | WO-2010/019781 A1 | 2/2010 |
| WO | WO-2010/080667 A1 | 7/2010 |
| WO | WO-2012/030331 A1 | 3/2012 |
| WO | WO-2013/041906 A1 | 3/2013 |
| WO | WO-2013/059609 A1 | 4/2013 |
| WO | WO-2019/226805 A1 | 11/2019 |

OTHER PUBLICATIONS

Whiteside, L. et al. (2011). "Methicillin-resistant *Staphylococcus aureus* in TKA Treated With Revision and Direct Intraarticular Antibiotic Infusion." Clin Orthop Relat Res, 469:26-33.

Schwerdt, C. et al. (2021). "The bactericidal effect of vancomycin is not altered by tranexamic acid, adrenalin, dexamethasone, or lidocaine in vitro." Scientific Reports, 11(1), 10739. 5 pages. https://doi.org/10.1038/s41598-021-90302-7.

Belay, E.S. et al. (2020). "Single-stage versus two-stage revision for shoulder periprosthetic joint infection: a systematic review and meta-analysis." J Shoulder Elbow Surg, 29: p. 2476-2486.

Cancienne, J.M. et al. (2018). "Risk Factors for Repeat Debridement, Spacer Retention, Amputation, Arthrodesis, and Mortality After Removal of an Infected Total Knee Arthroplasty With Spacer Placement." J Arthroplasty, 33(2): p. 515-520.

Chung, A.S. et al. (2019). "Two-Stage Debridement With Prosthesis Retention for Acute Periprosthetic Joint Infections." J Arthroplasty, 34(6): p. 1207-1213.

Cochran, A. et al. (2016). "Risk of Reinfection After Treatment of Infected Total Knee Arthroplasty." J Arthroplasty, 31: p. S156-S161.

De Beaubien, B.C. et al. (2019). "Local Instillation of Vancomycin and Tobramycin Combined with Negative Pressure Wound Therapy During 7-Day Two-Stage Arthroplasty Improves Clinical Outcomes." [Presentation slide]. AAOS 2019 Annual Meeting, Las Vegas, Nevada, United States. 1 page.

Ekpo, T.E. et al. (2012, Sep. 22). "Abbreviated Two-Stage Exchange Arthroplasty for Periprosthetic Joint Infection: 2 to 6 Year Results." [Poster presentation]. 31st Annual meeting of the European Bone and Joint Infection Society, Montreux, Switzerland. 1 page.

Finsterbusch, A. et al. (1970). "Bone and joint perfusion with antibiotics in the treatment of experimental staphylococcal infection in rabbits." J Bone Joint Surg Am, 52(7): p. 1424-1432.

Florschutz, A.V. et al. (2015). "Infection after primary anatomic versus primary reverse total shoulder arthroplasty." J Shoulder Elbow Surg, 24(8): p. 1296-1301.

Kalbian, I., et al. (2020). "Culture-negative periprosthetic joint infection: prevalence, aetiology, evaluation, recommendations, and treatment." Int Orthop, 44(7): p. 1255-1261.

Lescun, T.B. et al. (2000). "Continuous infusion of gentamicin into the tarsocrural joint of horses." Am J Vet Res, 61(4): p. 407-412.

Lescun, T.B. et al. (2006). "Treatment with continuous intrasynovial antimicrobial infusion for septic synovitis in horses: 31 cases (2000-2003)." J Am Vet Med Assoc, 228(12): p. 1922- 1929.

Lloyd, K.C. et al. (1988). "Effect of gentamicin sulfate and sodium bicarbonate on the synovium of clinically normal equine antebrachiocarpal joints." Am J Vet Res, 49(5): p. 650-657.

Lloyd, K.C., et al. (1988). "Plasma and synovial fluid concentrations of gentamicin in horses after intra-articular administration of buffered and unbuffered gentamicin." Am J Vet Res, 49(5): p. 644-649.

Nelson, G.N. et al. (2016). "Outcomes in the treatment of periprosthetic joint infection after shoulder arthroplasty: a systematic review." J Shoulder Elbow Surg, 25(8): p. 1337-1345.

Parvizi, J. et al. (2018). "The 2018 Definition of Periprosthetic Hip and Knee Infection: An Evidence-Based and Validated Criteria." J Arthroplasty, 33(5): p. 1309-1314.e2.

Paxton, E.S. et al. (2019). "Periprosthetic Infections of the Shoulder: Diagnosis and Management." J Am Acad Orthop Surg, 27(21): p. e935-e944.

Rabinowitz J. et al. (2020). "Utilization of Shoulder Arthroplasty in the United States—An Analysis of Current Trends and Future Predictions," in MUSC Siegling Day Department of Orthopaedic Research Day 2020. Seminars in Arthroplasty:JSES, 30: p. 200-209.

Schneider, R.K. et al. (1992). "Open drainage, intra-articular and systemic antibiotics in the treatment of septic arthritis/tenosynovitis in horses." Equine Vet J, 24(6): p. 443-9. [Abstract: 2 pages].

Shelly, M. et al. (2011). "Renal Toxicity Related to Antibiotic-Containing Orthopedic Cement." Pharmacokinetics and Adverse Drug Reactions. 2 pages.

Ure, K.J. et al. (1998). "Direct-exchange arthroplasty for the treatment of infection after total hip replacement. An average ten-year follow-up." J Bone Joint Surg Am, 80(7): p. 961-968.

Whitehair, K.J., et al. (1992). "Regional Limb Perfusion for Antibiotic Treatment of Experimentally Induced Septic Arthritis." Vet Surg, 21(5): p. 367-73. [Abstract: 2 pages].

Wroblewski, B.M. (1986). "One-stage Revision of Infected Cemented Total Hip Arthroplasty." Clin Orthop Relat Res, (211): p. 103-107.

Zavala, J.A. et al. (2012). "Management of deep infection after reverse total shoulder arthroplasty: a case series." J Shoulder Elbow Surg, 21(10): p. 1310-1315.

U.S. Appl. No. 16/513,599, filed Jul. 16, 2019, 2020-0038191.

U.S. Appl. No. 17/971,080, filed Oct. 21, 2022, US 20230041597.

(56) References Cited

OTHER PUBLICATIONS

PCT/US2024/16687, Feb. 21, 2024, WO 2024/178093.
PCT/US2024/16660, Feb. 21, 2024, WO 2024/178070.

* cited by examiner

SYSTEM AND METHOD FOR TREATMENT AND PREVENTION OF PERIPROSTHETIC JOINT INFECTIONS

CROSS-REFERENCE TO RELATED APPLICATIONS

This application claims the benefit of U.S. Provisional Patent Application No. 63/065,413 filed Aug. 13, 2020, the content of which is incorporated herein by reference.

BACKGROUND

Each year, over one million Americans undergo hip or knee arthroplasty (joint replacement surgery) to treat reduced mobility and joint pain. Moreover, Total Should Replacement (TSR) volume is growing rapidly. Periprosthetic joint infections (PJI), a debilitating and hard to treat complication, affects ~2% of this patient population. Individuals with hip or knee PJI have 6.5% mortality in the first year, a 3-fold increase over individuals the same age (2%).

Surgery with adjuvant systemic antibiotics is the foundation of PJI treatment surgical management of PJI however is complicated by the presence of a biofilm, a polysaccharide matrix generated by the bacteria, rendering them highly resistant to systemic antibacterial treatment. Metallic implants provide a site for biofilm formation and in most cases, implant removal is considered an essential part of surgical management to eradicate the infection. The intravenous (IV) administration of systemic antibiotics for PJI may not result in adequate therapeutic concentrations for eradication of biofilm at the site of infection. Achievement of locally therapeutic levels is crucial for clinical success; however, this is difficult or impossible due to the fact that most PJI pathogens are biofilm forming. Biofilm-encapsulated bacteria require minimum biofilm eradication concentrations (MBEC) of antibiotics that are several orders of magnitude (100 to 1000×) above the minimum inhibitory concentrations (MIC) sufficient to eradicate planktonic bacteria. Therapeutic target attainment at levels near the MBEC may not work via systemic routes of administration without significant risk of toxicity to other organ systems.

SUMMARY

Provided herein is a hip spacer comprising a body comprising a fluid inlet; a fluid outlet; and a femoral head aperture. Also provided herein is a hip spacer system comprising: the hip spacer; and a catheter in fluidic communication with the inlet of the hip spacer. Also provided herein is a hip spacer platform comprising: the hip spacer system; and a pump in fluidic communication with the catheter and the fluid outlet of the hip spacer. Also provided herein is a hip spacing kit comprising: two or more sizes of the hip spacer system; and a pump in fluidic communication with the catheter and the fluid outlet of the hip spacer.

Provided herein is a knee spacer comprising a body comprising a fluid inlet and a fluid outlet. Also provided herein is a knee spacer system comprising: the knee spacer; and a catheter in fluidic communication with the inlet of the knee spacer. Also provided herein is a knee spacer platform comprising: the knee spacer system; and a pump in fluidic communication with the catheter and the fluid outlet of the knee spacer. Also provided herein is a knee spacing kit comprising: two or more sizes of the knee spacer system; and a pump in fluidic communication with the catheter and the fluid outlet of the knee spacer.

Provided herein is a shoulder spacer comprising a body comprising a fluid inlet and a fluid outlet. Also provided herein is a shoulder spacer system comprising: the shoulder spacer; and a catheter in fluidic communication with the inlet of the shoulder spacer. Also provided herein is a shoulder spacer platform comprising: the shoulder spacer system; and a pump in fluidic communication with the catheter and the fluid outlet of the shoulder spacer. Also provided herein is a shoulder spacing kit comprising: two or more sizes of the shoulder spacer system; and a pump in fluidic communication with the catheter and the fluid outlet of the shoulder spacer.

Also provided herein is a method of treating periprosthetic joint infection, the method comprising: providing one of: a hip spacer platform as disclosed herein; a knee spacer platform as disclosed herein; and a shoulder (or reverse shoulder) spacer platform disclosed herein; supplying a medication to the pump to irrigate a location of the joint infection over a period of time.

In another aspect, embodiments of the present invention encompass spacer platform systems and methods for treating a patient presenting with an acute periprosthetic joint infection of a joint. Exemplary spacer platforms can include a spacer system having a spacer and a catheter, where the spacer and catheter are configured for detachable coupling. A spacer platform can also include a pump assembly that is configured for coupling with the catheter. In some embodiments, the spacer is configured for placement between a first implant and a second implant of a permanent joint prosthesis, where the first implant secured with a first bone of the joint and the second implant secured with a second bone of the joint. In some embodiments, the spacer includes a first surface configured for articulating engagement with the first implant, a second surface configured for fixed engagement with the second implant, an exposed surface disposed between the first surface and the second surface, and an inlet configured to receive a treatment fluid. In some embodiments, the first surface includes a first plurality of outlets in fluid connection with the inlet and the exposed surface includes a second plurality of outlets in fluid communication with the inlet, such that treatment fluid delivered into the inlet can flow out through the first plurality of outlets and to the first implant and out through the second plurality of outlets and into a joint space between the first implant and the second implant.

In some instances, the spacer system is a hip spacer system, the joint is a hip joint, the first implant is an acetabular cup, and the second implant is a femoral stem. In some instances, the spacer system is a knee spacer system, the joint is a knee joint, the first implant is a femoral implant, and the second implant is a tibial implant. In some instances, the spacer system is a shoulder spacer system, the joint is a shoulder joint, the first implant is a glenoid implant, and the second implant is a humeral stem. In some instances, the second surface of the spacer includes a plurality of fluted channels. In some instances, at least one of the fluted channels includes a plurality of fluid outlets. In some instances, the plurality of fluted channels are arrayed about a center axis of the spacer. In some instances, the plurality of fluted channels enable fluid flow under the spacer, between the spacer and the second implant. In some instances, the spacer is undersized relative to the first implant. In some instances, the spacer comprises a biocompatible polymer such as low-density polyethylene (LDPE), high-density polyethylene (HDPE), polypropylene (PP), polyvinyl chloride (PVC) polystyrene (PS) nylon, polytetrafluoroethylene, a thermoplastic polyurethane (TPU), acetyl copolymer, silicone, polyether ether ketone (PEEK), a polyurethane, a biocompatible elastomer, or ultrahigh molecular weight polyethylene (UHMWPE).

In still another aspect, embodiments of the present invention encompass methods for treating a patient presenting with an acute periprosthetic joint infection of a joint. Exemplary methods can include removing one or more prosthetic components disposed between a first implant of secured with a first bone of the joint and a second implant secured with a second bone of the joint, placing a spacer of a spacer system between the first implant and the second implant, the spacer system having the spacer, a catheter, and a pump assembly, where the spacer and catheter are configured for detachable coupling, and where the pump assembly is configured for coupling with the catheter. Methods can also include delivering a treatment fluid from the pump, through the catheter, into an inlet of the spacer, and out through a first plurality of outlets at a first surface of the spacer to the first implant, and out through a second plurality of outlets at an exposed surface of the spacer and into a joint space between the first implant and the second implant. In some cases, the spacer system is a hip spacer system, the joint is a hip joint, the first implant is an acetabular cup, and the second implant is a femoral stem. In some cases, the spacer system is a knee spacer system, the joint is a knee joint, the first implant is a femoral implant, and the second implant is a tibial implant. In some cases, the spacer system is a shoulder spacer system, the joint is a shoulder joint, the first implant is a glenoid implant, and the second implant is a humeral stem. In some cases, the second surface of the spacer includes a plurality of fluted channels. In some cases, at least one of the fluted channels includes a plurality of fluid outlets. In some cases, the plurality of fluted channels are arrayed about a center axis of the spacer. In some cases, the spacer is undersized relative to the first implant. In some cases, the spacer includes a biocompatible polymer such as low-density polyethylene (LDPE), high-density polyethylene (HDPE), polypropylene (PP), polyvinyl chloride (PVC) polystyrene (PS) nylon, polytetrafluoroethylene, a thermoplastic polyurethane (TPU), acetyl copolymer, silicone, polyether ether ketone (PEEK), a polyurethane, a biocompatible elastomer, or an ultrahigh molecular weight polyethylene (UHMWPE). In some cases, the pump assembly is a negative pressure wound therapy pump assembly.

In yet another aspect, embodiments of the present invention encompass methods of treating a patient presenting with an acute periprosthetic joint infection of a joint, where methods may include removing one or more prosthetic components disposed between a first implant of secured with a first bone of the joint and a second implant secured with a second bone of the joint, and placing a spacer of a spacer system between the first implant and the second implant. The spacer system can include the spacer, a catheter, and a pump assembly, and the spacer and catheter can be configured for detachable coupling. The pump assembly can be configured for coupling with the catheter. Methods may also include delivering an antibiotic treatment fluid from the pump, through the catheter, into an inlet of the spacer, and out through a first plurality of outlets at a first surface of the spacer to the first implant, out through a second plurality of outlets at an exposed surface of the spacer and into a joint space between the first implant and the second implant, and out through a third plurality of outlets at a second surface of the spacer, the third plurality of outlets disposed within one or more fluted channels of the second surface so as to provide fluid flow between the spacer and the second implant. In some cases, the antibiotic treatment fluid is provided continuously or periodically to the patient over a treatment period of 7 days or more. In some cases, the catheter remains attached with the spacer throughout the treatment period.

In still yet another aspect, embodiments of the present invention encompass spacer platforms for treating a patient presenting with an acute periprosthetic joint infection of a joint, where spacer platforms can include a spacer system having a spacer and a catheter, and where the spacer and catheter are configured for detachable coupling. In some cases, a pump assembly that is configured for coupling with the catheter to deliver a treatment fluid to the joint. In some cases, the spacer includes a first surface configured for articulating engagement with the first implant, a second surface configured for fixed engagement with the second implant, an exposed surface disposed between the first surface and the second surface, and an inlet configured to receive the treatment fluid. In some cases, the spacer is configured with a plurality of outlets to deliver the treatment fluid into the joint.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
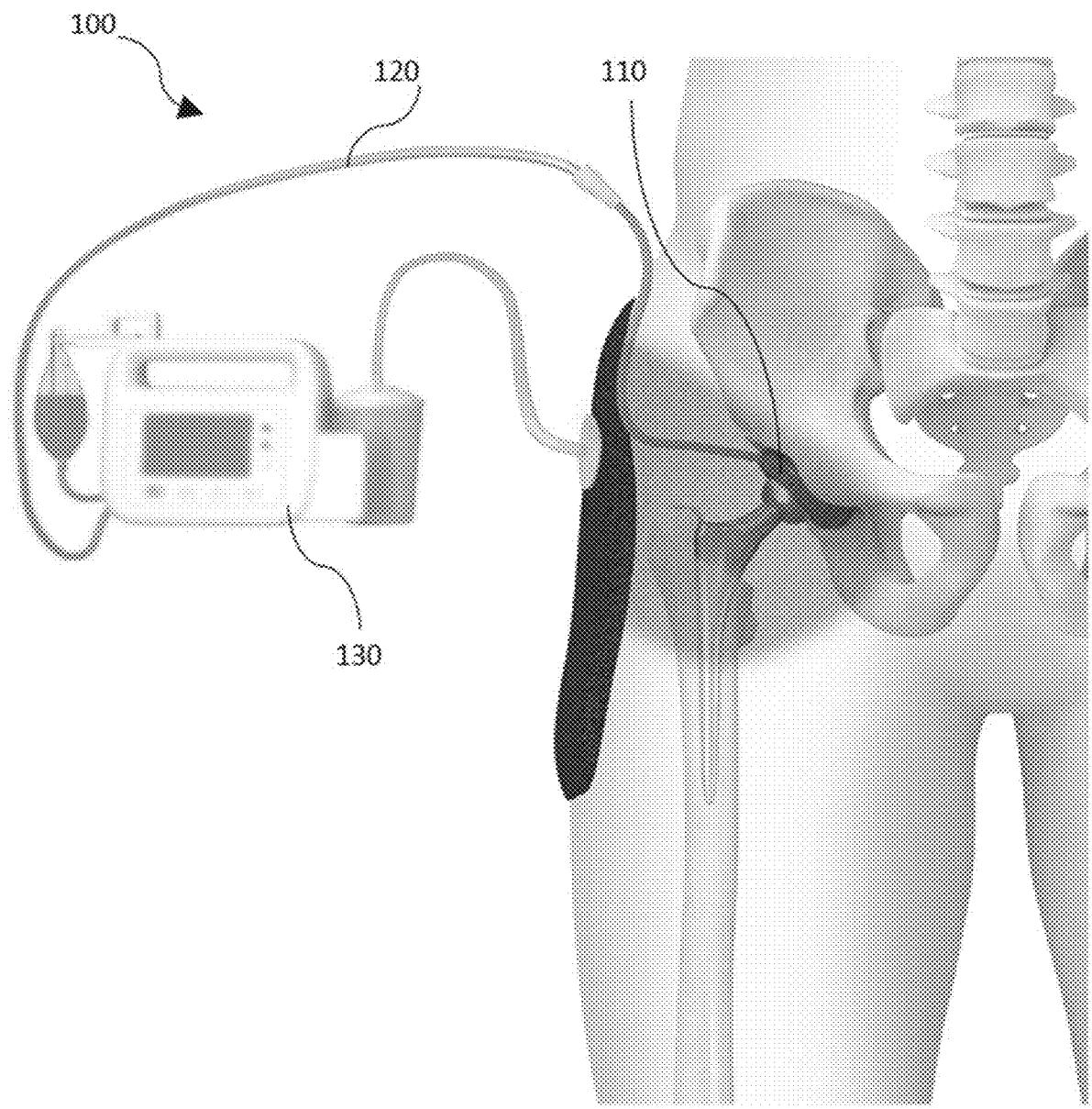
FIG. 1 shows a front-view illustration of an exemplary hip antibiotic irrigation platform, per an embodiment herein.

A number of surgical interventions are used to treat periprosthetic joint infection (PJI). The standard of care (SOC) for treatment of chronic PJI may include a two-stage exchange arthroplasty: surgical removal of the infected implant, aggressive debridement and two-stage exchange arthroplasty with administration of systemic antibiotics. Stage 1 of the procedure includes removal of the infected prosthesis and implantation of a temporary antibiotic impregnated cement spacer with adjuvant administration of systemic antibiotic therapy as needed, typically for a period of at least 6 weeks. Stage 2 of the procedure is performed when patients are considered infection free and includes removal of the temporary spacer and implantation of a new permanent prosthesis. Irrigation, and irrigation and debridement with implant retention, is an attractive alternative due to decreased patient morbidity associated with resection arthroplasty.

Prosthesis retention is an attractive alternative due to overall decreased patient morbidity. For acute cases, select patients retain their implants as the biofilm does not have time to mature. Acute cases with well-fixed implants and a known pathogen can be treated with Debridement, Antibiotics and Implant Retention (DAIR). The DAIR procedure includes a radical debridement and irrigation of the infected joint, often with replacement of the modular implant components (i.e. knee: tibial polyethylene, hip: acetabular polyethylene liner and metal or ceramic femoral head).

Many factors influence the ultimate surgical management chosen for a given patient. Examples of these factors could include duration of symptoms, joint age (early, delayed, or late), infecting pathogen and its susceptibility pattern, prosthesis stability, and the patient's preexisting medical comorbidities. Other factors, such as the quality of the periprosthetic soft tissue, the options available for successful reconstructive surgery after resection arthroplasty, the expertise of the clinician(s), and the patient's preferences, also influence the surgical management. Clinical guidelines for PJI treatment have been published by the Infectious Diseases Society of America (IDSA). The guidelines state that implant retention strategies can be used in acute PJI where the biofilm does not have time to mature before surgical intervention.

Research shows the timeline for biofilm formation may be dependent on a number of host related factors and bacterial species, with animal studies showing biofilm can develop rapidly after bacterial exposure, in minutes to hours.

The potential for biofilm formation in minutes to hours may contribute to the limited success of implant retention treatments, as biofilm may already be attached to the retained implants even in acute cases, allowing continued dispersion of bacteria from the biofilm remaining after the irrigation and debridement procedure. Continuous local antibiotic irrigation delivered by systems and methods disclosed herein have the potential to eradicate any remaining biofilm on retained implants after irrigation and debridement, significantly improving success rate of implant retention strategies for treating PJI.

Many issues exist with current implant retention treatments. First, systemic antibiotic concentrations are not sufficient to eradicate biofilm. For example, when antibiotics are administered systemically, concentrations at the infection site are much lower than serum concentrations: local vancomycin HCl concentration is 10% to 60% and local tobramycin sulfate concentration is 9% to 13% of serum concentration. Achievement of locally therapeutic levels is crucial for clinical success; however, this is difficult due to the fact that most PJI pathogens are biofilm forming. Biofilm-encapsulated bacteria require minimum biofilm eradication concentrations (MBEC) of antibiotics that are several orders of magnitude (100 to 1000×) above the minimum inhibitory concentrations (MIC) sufficient to eradicate planktonic bacteria. Therapeutic target attainment at levels greater than the MBEC is impossible via systemic routes of administration without significant risk of toxicity to other organ systems.

Second, while current guidelines dictate 4-6 weeks of IV antibiotics and up to one year of oral antibiotics to eradicate the infection, long term antibiotic use increases development of antibiotic resistant organisms.

As such, provided herein are rapid and effective local infection therapy methods, systems, and devices that significantly reduce the mortality, morbidity, and the cost of care in rare musculoskeletal infections. Continuous delivery of antibiotic therapy locally, at the infection site, reduces edema and provides antibiotic irrigation, significantly improving outcomes while reducing the need for systemic antibiotics.

Such approaches can involve a spacer that is placed between permanent implants of a prosthesis, for a temporary period of time. In some cases, such permanent implants may not yet be infected between the implant and the bone, during the first 2-4 weeks following their implantation. Such implants remain well-fixed in bone. If a surgeon can detect infection early after its onset, the infection can be treated without removing the two permanent implants by placing a spacer therebetween temporarily, while temporarily irrigating the surrounding soft tissue to achieve certain clinical advantages. In such procedures, the surgeon may remove certain modular components of the prosthetic implant system, and replace them with an interpositional spacer as disclosed herein, for a period of time (e.g. having a duration within a range from about 3 days to about 3 weeks). Following the irrigation treatment period, the interpositional spacer can then be removed, and replaced with one or more permanent prosthetic replacement components.

Interpositional spacers (and related systems and methods) as disclosed herein are well suited for use in treating patients presenting with acute periprosthetic joint infection (PJI), for example as part of a Debridement, Antibiotics and Implant Retention (DAIR) procedure.

Hip Spacer Platforms, Systems, and Devices

Figure 2:
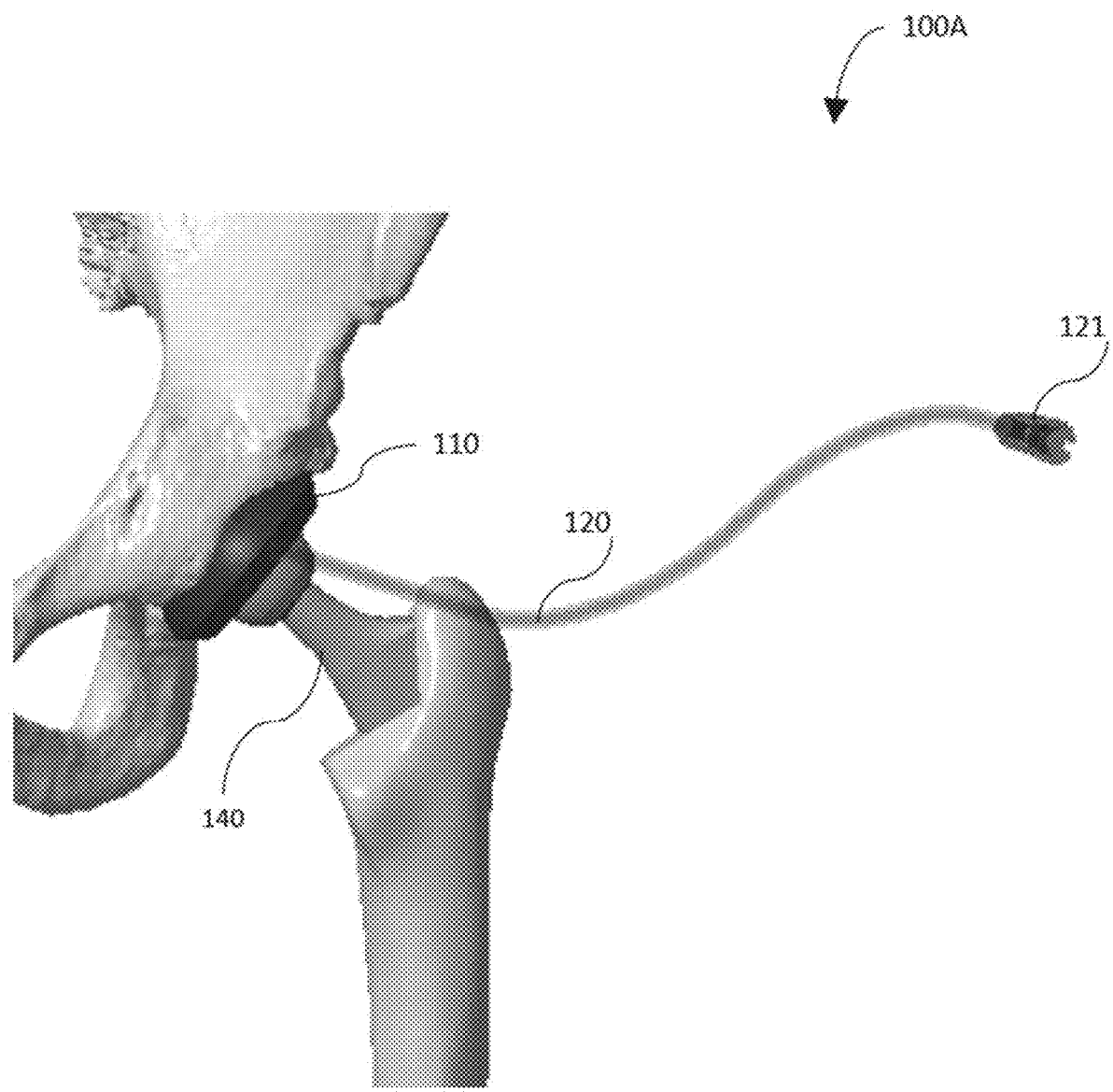
FIG. 2 shows a front-view illustration of an exemplary hip antibiotic irrigation system installed about a human hip joint, per an embodiment herein.
Figure 3A:
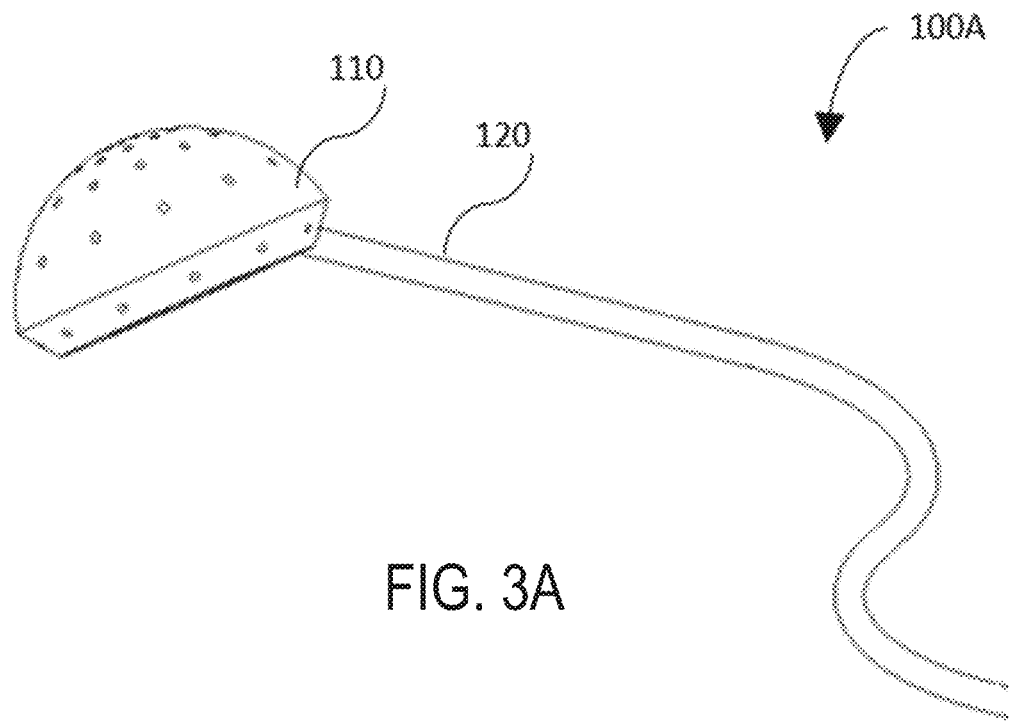
FIG. 3A shows a front-view illustration of an exemplary hip spacer system, per an embodiment herein.
Figure 3B:
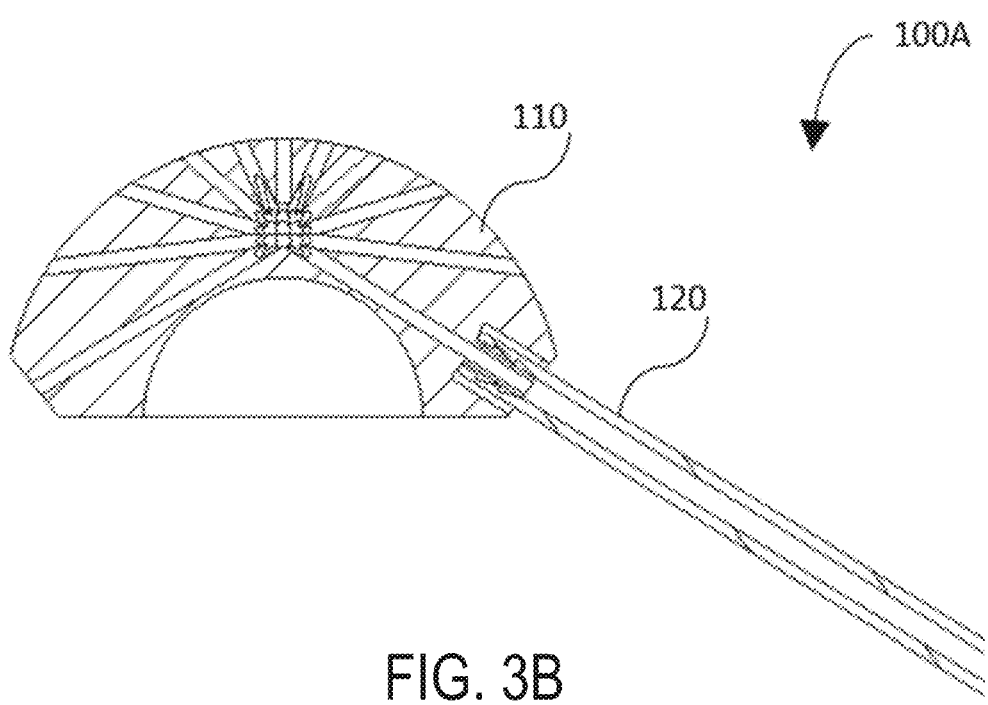
FIG. 3B shows a cross-sectioned front-view illustration of an exemplary hip spacer system, per an embodiment herein.

Provided herein, per FIG. 1, is a hip spacer platform 100 comprising a hip spacer system 100A (FIG. 2) and a negative pressure wound therapy pump 130. It is understood that the instant disclosure is not limited to a NPWT pump, and that any infusion and vacuum pump may be used. For example, embodiments encompass hip spacer platforms which include a vacuum pump with gravity infusion. In some embodiments, per FIGS. 2-5D, the hip spacer system 100A comprises a hip spacer 110 and a catheter 120. In some embodiments, per FIGS. 4A-4D, the hip spacer 110 comprises a fluid inlet 111, one or more fluid outlets 112, and a femoral head aperture 113. In some embodiments, the catheter 120 is in fluidic communication with the fluid inlet 111 of the hip spacer 110. In some embodiments, the negative pressure wound therapy (NPWT) pump 130 is in fluidic communication with the catheter 120 and the fluid outlet(s) 112 of the hip spacer 110. In some embodiments, the catheter 120 is coupled to the NPWT pump via a connection 121. Also provided herein is a hip spacing kit comprising two or more sizes of the hip spacer system 100A and the negative pressure wound therapy pump 130 (or any infusion and vacuum pump), so as to accommodate various patient anatomies. Hence, in some cases, a hip spacer platform or hip spacing kit may or may not include a NPWT pump.

As shown in FIGS. 4A-4D, in some embodiments, the hip spacer 110 comprises a single fluid inlet 111 and a plurality of fluid outlets 112. Alternatively, in some embodiments, the hip spacer 110 comprises 1, 2, 3, 4, 5, 6, 7, 8, 9, 10, or more fluid inlets 111. Alternatively, in some embodiments, the hip spacer 110 comprises 1, 2, 3, 4, 5, 6, 8, 10, 15, 20, 25, 30, 35, 40, 45, 50, 55, 60, 65, 70, 75, 80 or more fluid outlets 112. In some embodiments, an inner diameter of the fluid inlet 111 is equal to an inner diameter of the fluid outlet(s) 112. In some embodiments, an inner diameter of the fluid inlet 111 is greater than an inner diameter of the fluid outlet(s) 112. In some embodiments, an inner diameter of the fluid inlet 111 is less an inner diameter of the fluid outlet(s) 112. In some embodiments, the location of the fluid inlet 111 is specified to be closer to a standard incision location.

Figure 4A:
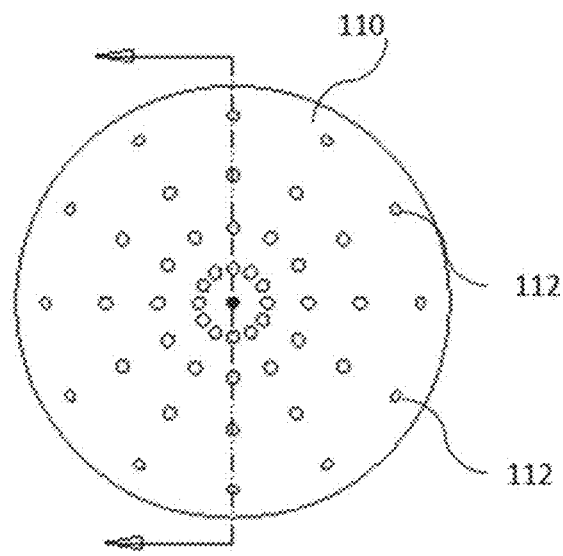
FIG. 4A shows a top-view illustration of an exemplary hip spacer, per an embodiment herein.
Figure 4B:
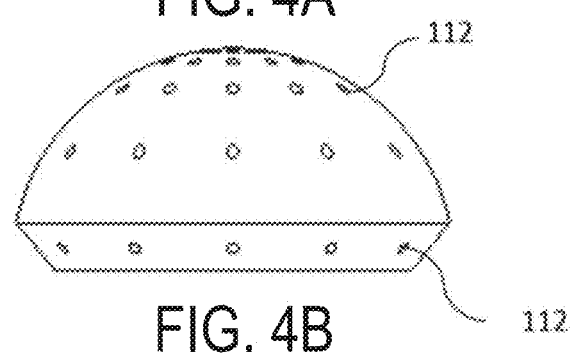
FIG. 4B shows a front-view illustration of an exemplary hip spacer, per an embodiment herein.
Figure 4D:
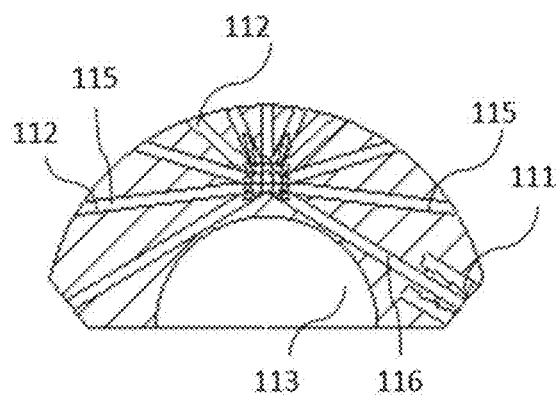
FIG. 4D shows a cross-sectioned front-view illustration of an exemplary hip spacer, per an embodiment herein.
Figure 4C:
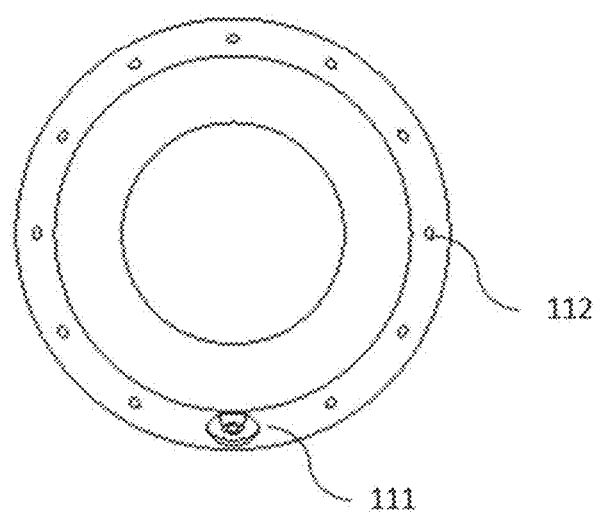
FIG. 4C shows a bottom-view illustration of an exemplary hip spacer, per an embodiment herein.

In some embodiments, as shown in FIG. 4D, the fluid inlet 111 is in fluidic communication with the fluid outlets 112 via an inlet channel 116 and one or more outlet channels 115. In some embodiments, each outlet channel 115 corresponds to a fluid outlet 112. In some embodiments, one or more outlet channels 115 each correspond to one or more fluid outlets 112. In some embodiments, the outlet channels 115 are configured in a polar array about a center of the hip spacer 110. In some embodiments, the fluid outlets 112 are arranged in a polar array about a center of the hip spacer 110. In some embodiments, the fluid outlets 112 are arranged in a polar array about a center of the hip spacer 110 in a series of radial and circular axes, wherein the radial axes intersect and wherein the circular axes are concentric. In some embodiments, the hip spacer 110 comprises 2, 4, 6, 8, 10, 12, 14, 16, 18, 20, 22, 24 or more radial axes. In some embodiments, the hip spacer 110 comprises 2, 4, 6, 8, 10, 12, 14, 16, 18, 20, 22, 24 or more circular axes. As shown, in some embodiments, the fluid outlets 112 are evenly arrayed about the hip spacer 110. Alternatively, the outlet channels 112 may be unevenly arrayed about the hip spacer 110. Alternatively, in some embodiments, the fluid outlets 112 are arranged in a rectilinear array. Further, in some embodiments, as shown, the inlet channel 116 and each of the outlet channels 115 intersect. In some embodiments, the inlet channel 116 and each of the outlet channels 115 intersect at a center axis of the hip spacer 110. In some embodiments, two or more of the fluid outlets 112 are concentric. In some embodiments, per FIGS. 4D, 5A and 5B, the hip spacer 110 mates with a retained femoral implant 140 (e.g., femoral stem in FIG. 5A, femoral head in FIG. 5B). In some embodiments, the femoral head aperture 113 of the hip spacer 110 mates with the retained femoral implant 140. In some embodiments, the hip spacer 110 articulates about the retained femoral implant 140. As shown, in some embodiments, the femoral head aperture 113 has a concave hemispherical shape. In some embodiments, the hip spacer 110 is disposed about a femoral head. Further as shown, the hip spacer 110 comprises a single uniform body. Alternatively, in some embodiments, the hip spacer 110 comprises two or more bodies that are removably coupled. Alternatively, in some embodiments, the hip spacer 110 comprises two or more components that are removably coupled, wherein the femoral head aperture 113 is multi-hemispherical. In some embodiments, at least a portion of an outer surface of the hip spacer 110 is hemispherical.

With continuing reference to FIG. 4D, it is understood that in some embodiments the total volume defined by the outlet channels 115 is less than the volume of a bolus or discrete amount of medicament or fluid delivered therethrough (which may be part of a periodic delivery regimen). Relatedly, the total volume defined by the outlet channels 115 can be minimized so that antibiotics or other fluids administered to the patient via the spacer are not retained by the spacer, and hence the spacer does not operate as a reservoir. This approach can maximize the amount of fluid that is delivered or exiting the spacer, and minimize the amount of fluid that is retained within the spacer. Hence, for example, if 50 cc of fluid is provided to the spacer, the total volume defined by the outlet channels can be less than 50 cc. This principle regarding total volume of outlet channels can also apply to knee spacer and/or shoulder spacer embodiments disclosed herein.

In some embodiments, the catheter is removably coupled to the fluid inlet 111 of the hip spacer 110. In some embodiments, the fluid inlet 111 of the hip spacer 110 comprises a luer taper, a barb fitting, or both to removably couple to the catheter. In some embodiments, the fluid inlet 111 of the hip spacer 110 is configured to couple to the catheter intra-operatively. In some embodiments, the catheter is permanently coupled to the fluid inlet 111 of the hip spacer 110. In some embodiments, the hip spacer system 100A further comprises a sterile packaging enclosing the hip spacer 110. In some embodiments, the sterile packaging comprises a double sterile barrier for introduction into the sterile field.

In some embodiments, the hip spacer platform 100 is configured to be implanted during a short-period of time. In some embodiments, the hip spacer 110 provides local irrigation, drug administration, or both. In some embodiments, the fluid inlet 111 and the fluid outlet(s) 112 of the hip spacer 110 provide local irrigation, drug administration, or both. In some embodiments, the hip spacer 110 is made of a biocompatible polymer. In some embodiments, the biocompatible polymer is a synthetic polymer. In some embodiments, the synthetic polymer is low-density polyethylene (LDPE), high-density polyethylene (HDPE), polypropylene (PP), polyvinyl chloride (PVC) polystyrene (PS) nylon, polytetrafluoroethylene, or a thermoplastic polyurethane (TPU). In some cases, a biocompatible polymer is acetyl copolymer (e.g. Delrin® or Celcon®), silicone, polyether ether ketone (PEEK), a polyurethane, including a flexible polyurethane, a biocompatible elastomer, or a ultrahigh molecular weight polyethylene (UHMWPE). In some embodiments, the hip spacer 110 is at least partially rigid. In some embodiments, the hip spacer 110 is at least partially flexible. In some embodiments, at least a portion of the hip spacer 110 has a modulus of elasticity of about 1 GPa to about 300 GPa.

In some embodiments, the hip spacer is configured to be positioned between the femoral head and acetabular cup of a permanent hip prosthesis. In some embodiments, the hip spacer is configured to be positioned between the femoral stem and acetabular cup of a permanent hip prosthesis with the prosthetic femoral removed. In both cases, the hip spacer has an additional function of protecting the surfaces of the prosthetic components during irrigation or treatment.

Figure 5A:
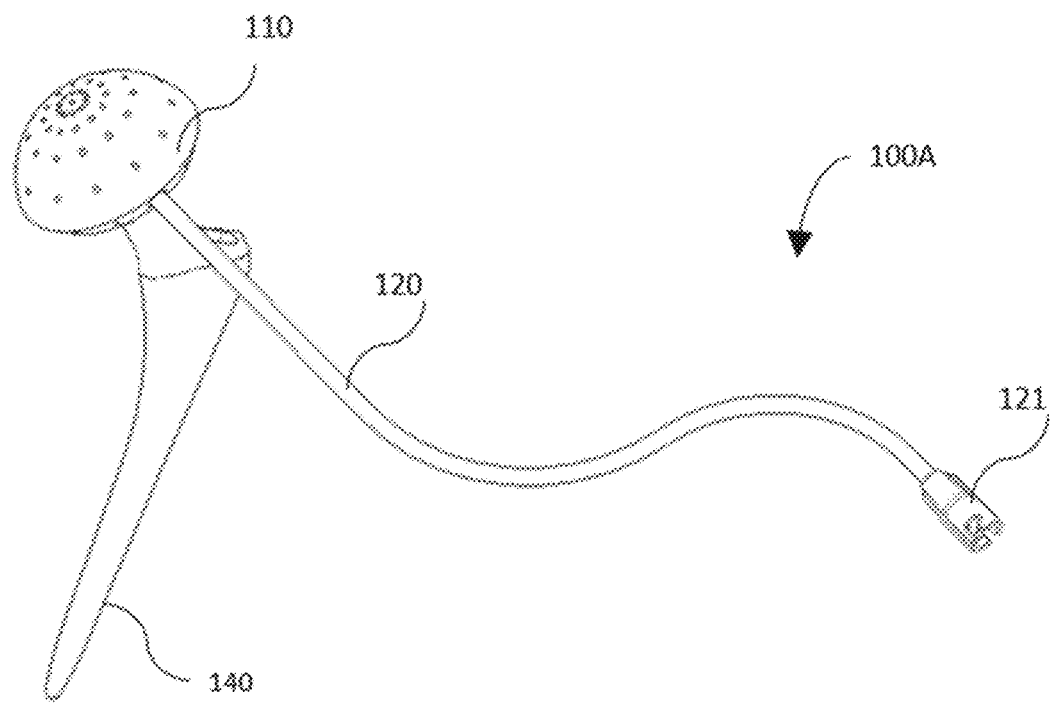
FIG. 5A shows a front-left perspective illustration of an exemplary hip spacer system coupled to a femoral stem, per an embodiment herein.
Figure 5B:
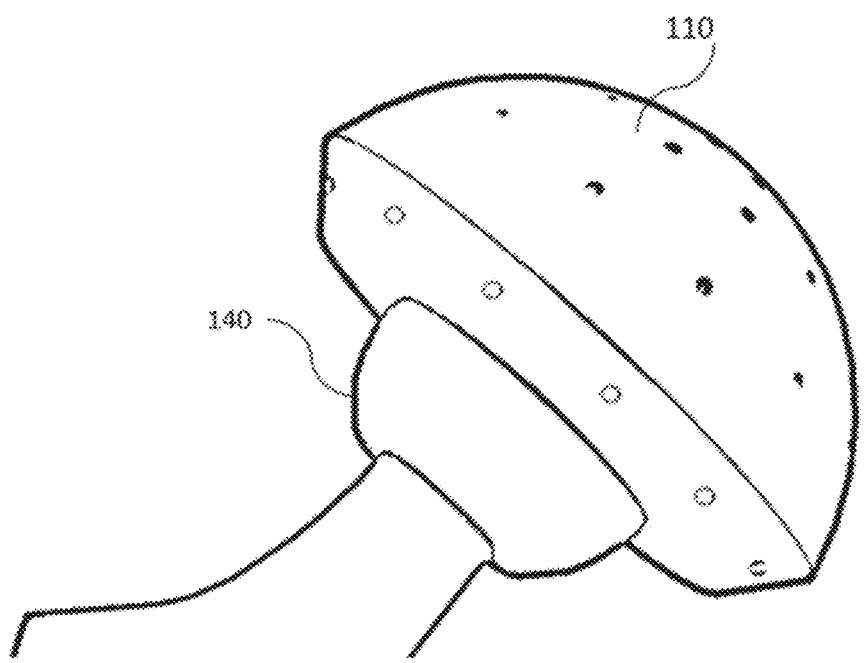
FIG. 5B shows a front-view illustration of an exemplary hip spacer system coupled to a femoral stem, per an embodiment herein.
Figure 5C:
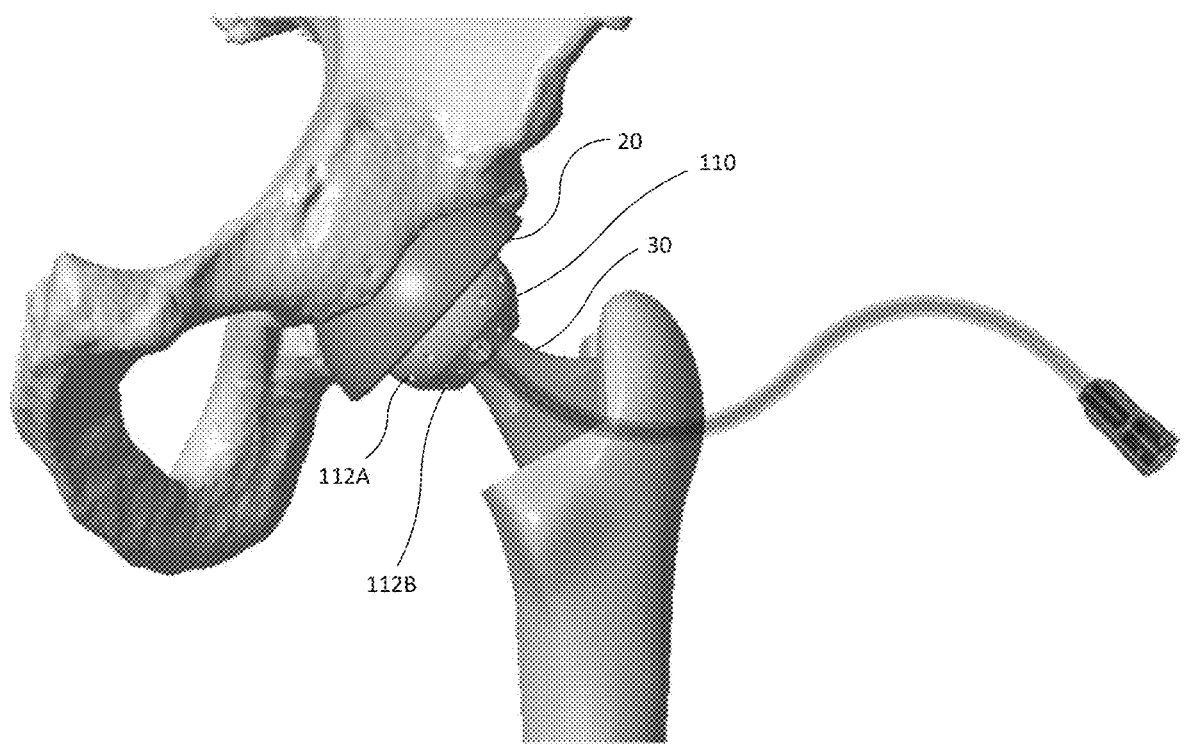
FIGS. 5C to 5K depict aspects of exemplary hip spacer systems, according to embodiments of the present invention.

As depicted in FIG. 5C, a hip spacer 110 can be placed between an acetabular cup 20 and a femoral stem 30 of a permanent hip prosthesis. In some instances, the acetabular cup 20 and/or the femoral stem can include or be fabricated from titanium. Fluid outlets may be positioned all over the hip spacer. For example, fluid outlets 112A may be on the spacer surface that contacts the cup 20. In this way, antibiotic or other materials can be provided into the acetabular cup 20, which itself may have holes in it, so as to facilitate the flow or delivery of antibiotic or other materials to acetabular bone. Fluid outlets 112B may be on the exposed surface of the spacer 110. Outlets 112B can facilitate the flow of treatment fluid to joint space between the first and second implants (20, 30). Hip spacer 110 can also include outlets which facilitate the flow of treatment fluid to spaces between the spacer and the second implant 30, and such flow may also be facilitated by the presence of fluted channels on the underside of the spacer. In the embodiment depicted in FIG. 5C, the hip spacer 110 can be used in a situation where the original prosthetic included a metal cup or shell which is attached with the acetabular bone, a liner (e.g. plastic) which is disposed within the metal cup or shell, a spherical head which articulates against or otherwise engages the liner, and stem or trunnion which is coupled with the spherical head or ball, and the surgical procedure involves removing the liner and spherical head, and temporarily inserting therefore the hip spacer 110. In contrast, the hip spacer 110 depicted in FIG. 3A (which is shown as less than hemispherical) can be used when the stem and spherical head of the original prosthetic are retained, and only the liner or liner and cup are removed.

Figure 5D:
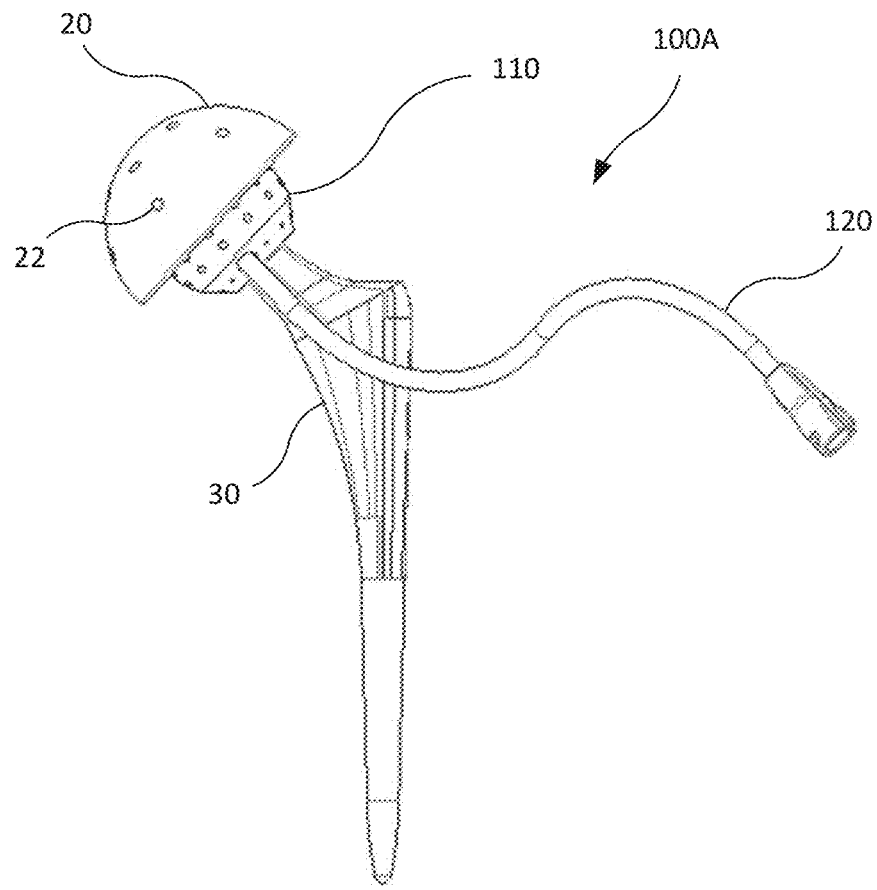
Figure 5E:
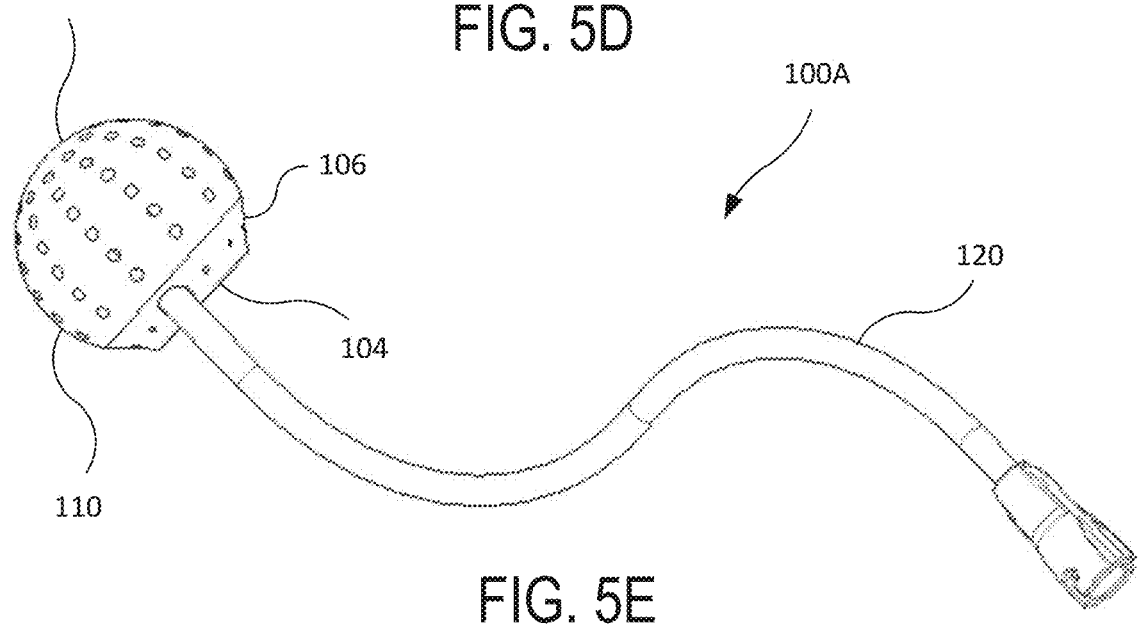
Figure 5F:
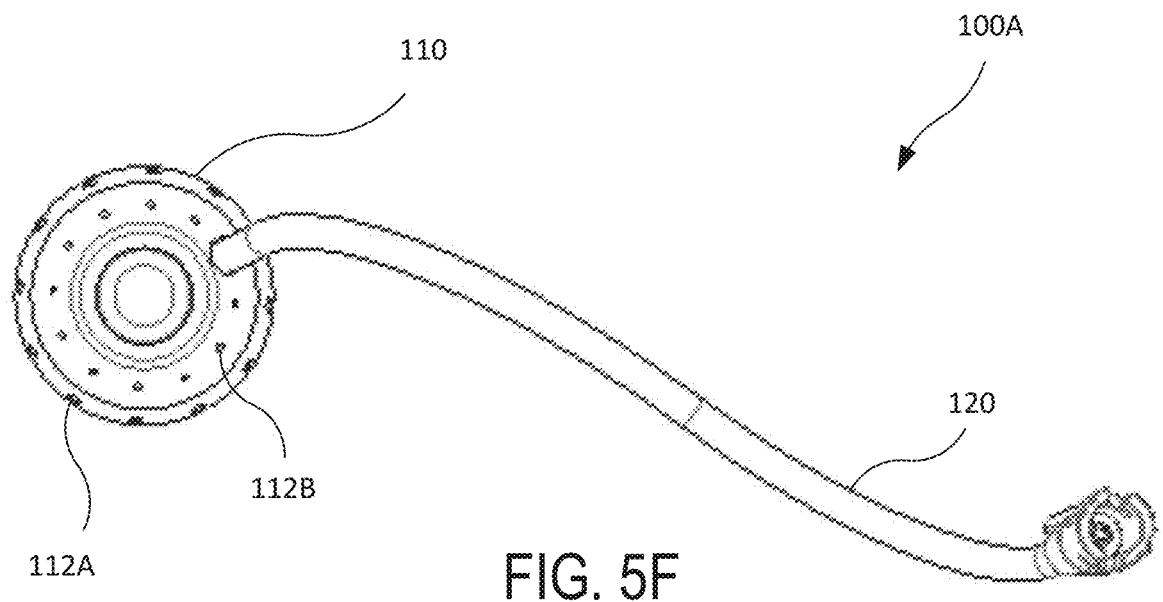
Figure 5G:
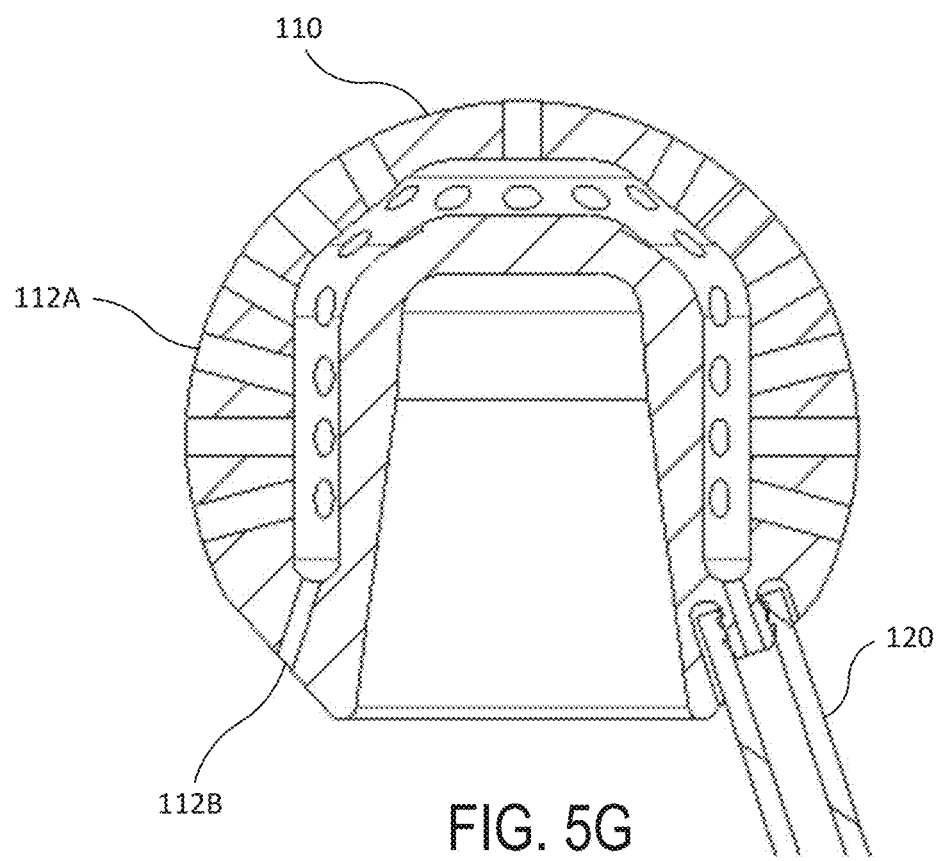
Figure 5H:
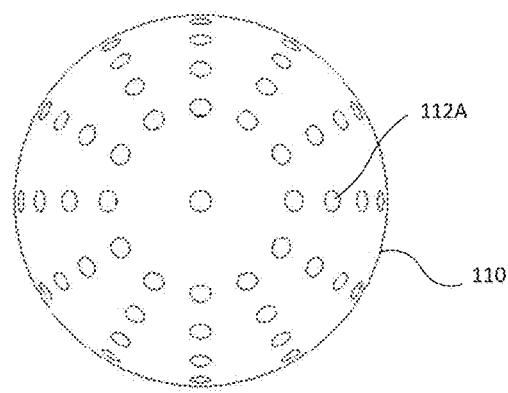
Figure 5J:
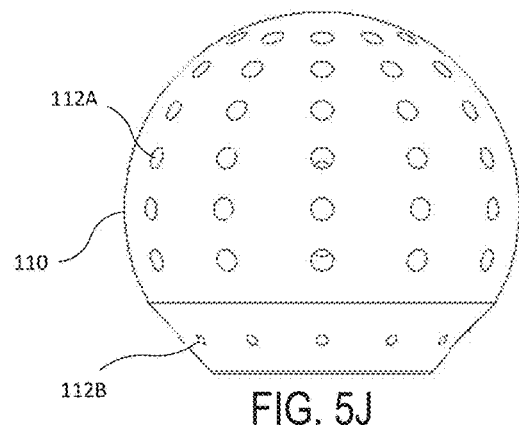
Figure 5I:
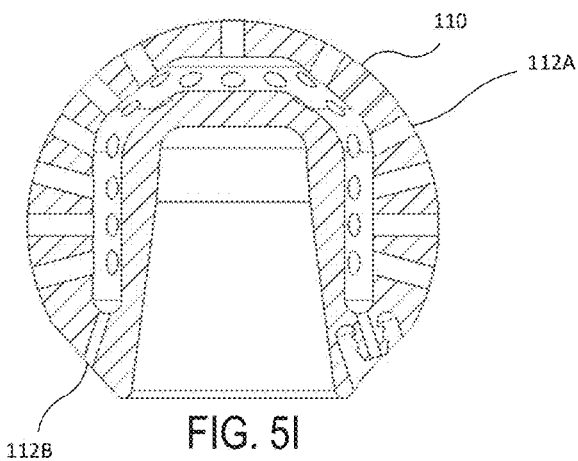
Figure 5K:
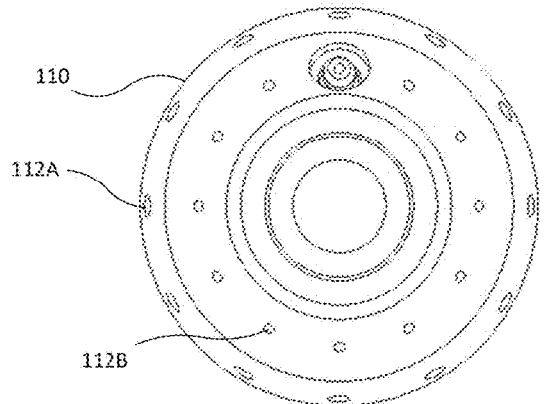

As shown in FIGS. 5D and 5E, a hip spacer system 100A can include a hip spacer 110 and a catheter 120. The hip spacer 100 can be coupled with a retained femoral stem 30 and acetabular cup 20 of a permanent hip prosthesis. As shown here, acetabular cup 20 includes one or more fluid outlets or apertures 22 whereby fluid provided via the spacer 110 can flow therethrough and toward acetabular bone. Spacer 100 includes a first surface 102 configured for articulating engagement with the first implant 20, a second surface 104 configured for fixed engagement with the second implant 30, and an exposed surface 106 disposed between the first surface 102 and the second surface 104. As shown in FIG. 5F, hip spacer system 100A can include a hip spacer 110 and a catheter 120, and as shown in the cross-section view of FIG. 5G, surfaces of the spacer 110 can include apertures 112A and 112B through which treatment fluid may flow. As shown in the top view of FIG. 5H, the cross-section view of FIG. 5I, the side view of FIG. 5J, and/or the bottom view of FIG. 5K, a hip spacer 110 can include apertures 112A and 112B through which treatment fluid may flow.

Knee Spacer Platforms, Systems, and Devices

Figure 6:
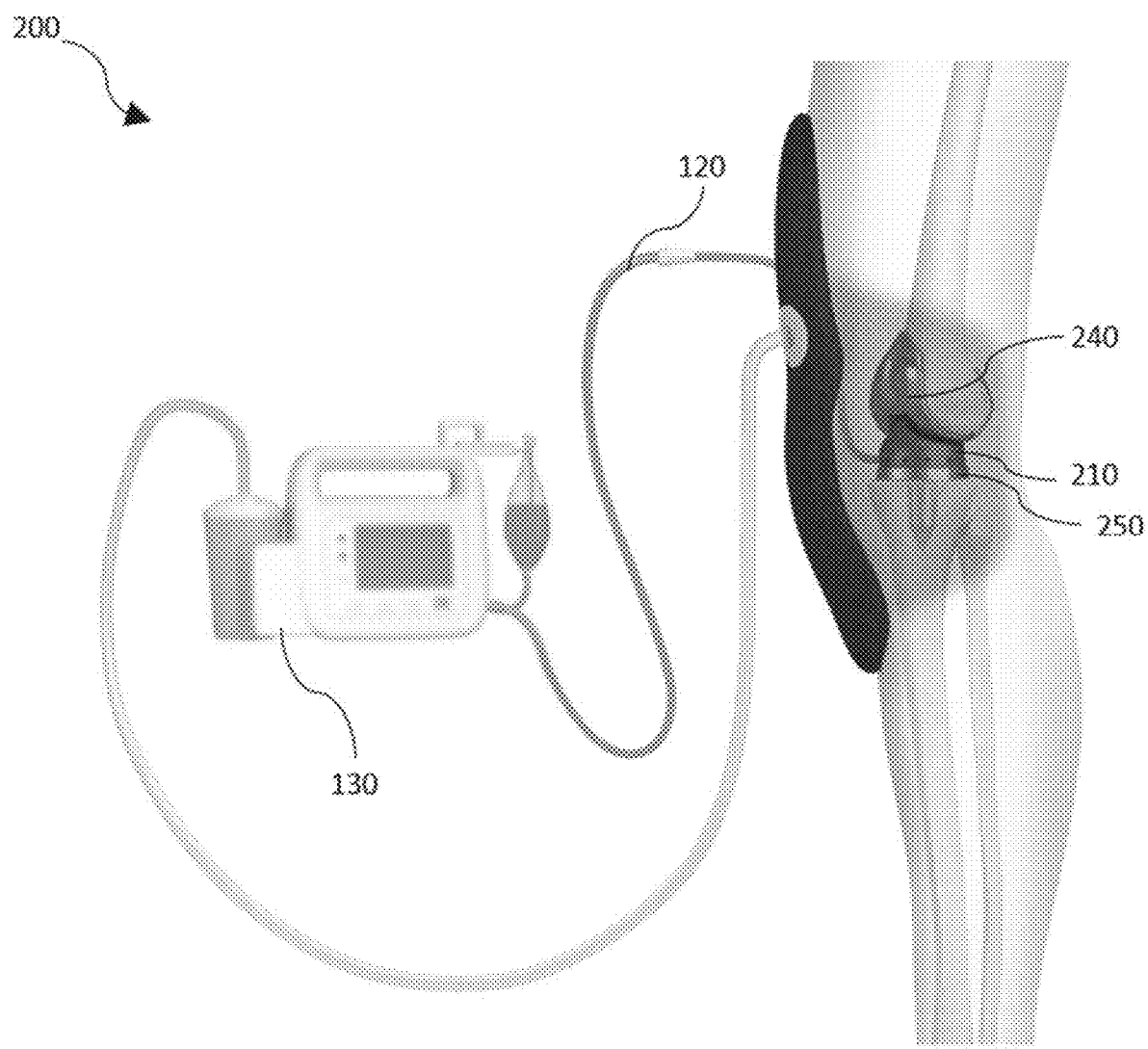
FIG. 6 shows a front-view illustration of an exemplary knee antibiotic irrigation platform, per an embodiment herein.
Figure 7:
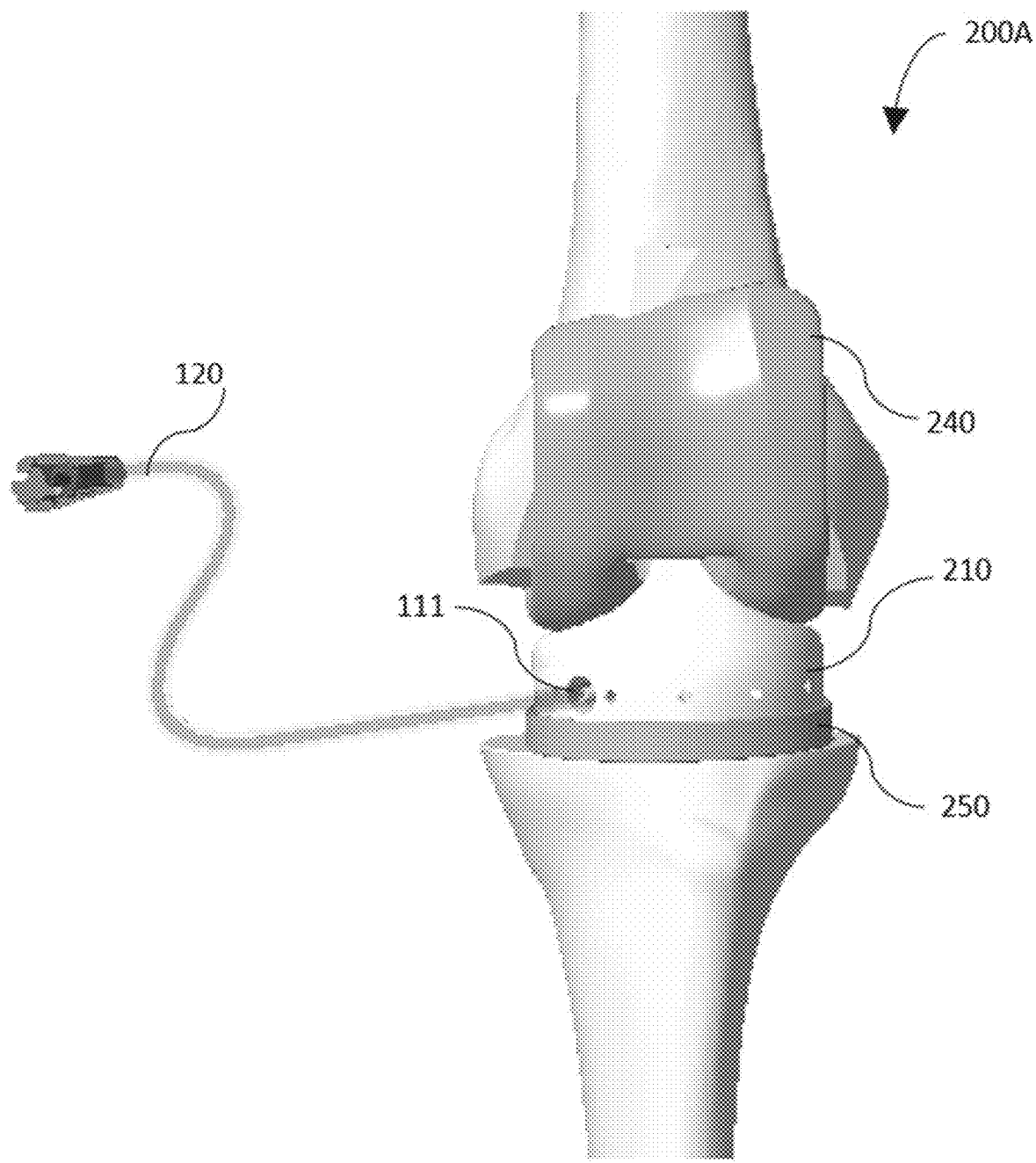
FIG. 7 shows a front-view illustration of an exemplary knee antibiotic irrigation system installed about a human knee joint, per an embodiment herein.
Figure 8A:
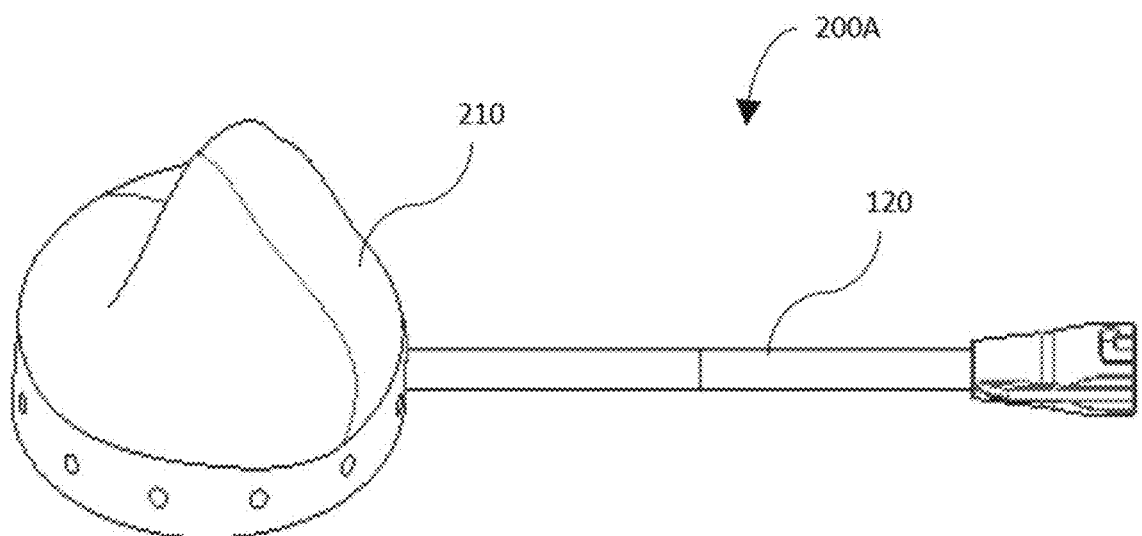
FIG. 8A shows a front-top perspective illustration of an exemplary knee spacer system coupled to a femoral stem, per an embodiment herein.
Figure 8B:
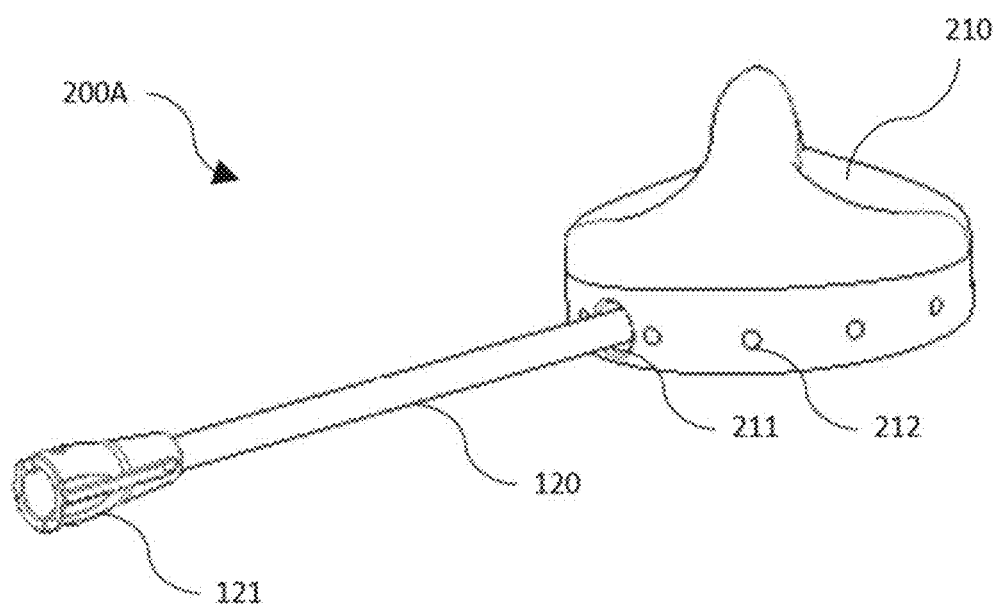
FIG. 8B shows a front-top-left perspective view illustration of an exemplary knee spacer system coupled to a femoral stem, per an embodiment herein.

Provided herein, per FIG. 6, is a knee spacer platform 200 comprising a knee spacer system 200A (FIG. 7) and a negative pressure wound therapy pump 130. It is understood that the instant disclosure is not limited to a NPWT pump, and that any infusion and vacuum pump may be used. For example, embodiments encompass knee spacer platforms which include a vacuum pump with gravity infusion. In some embodiments, per FIGS. 7-8B, the knee spacer system 200A comprises a knee spacer 210 and a catheter 120. In some embodiments, per FIGS. 8A-9C, the knee spacer 210 comprises a fluid inlet 211, one or more fluid outlets 212, and a femoral component post 213. In some embodiments, the catheter 120 is in fluidic communication with the fluid inlet 211 of the knee spacer 210. In some embodiments, the negative pressure wound therapy pump 130 is in fluidic communication with the catheter 120 and the fluid outlet(s) 212 of the knee spacer 210. In some embodiments, the catheter 120 is coupled to the NPWT pump via a connection 121. Also provided herein is a knee spacing kit comprising two or more sizes of the knee spacer system and the negative pressure wound therapy pump (or any infusion and vacuum pump), so as to accommodate various patient anatomies. Hence, in some cases, a knee spacer platform or knee spacing kit may or may not include a NPWT pump.

Provided herein, per FIG. 6, is a knee spacer platform 200 comprising a knee spacer system 200A and a negative pressure wound therapy pump 130. In some embodiments, per FIGS. 7-8B, the knee spacer system 200A comprises a knee spacer 210 and a catheter 120. In some embodiments, per FIGS. 9A-9C, the knee spacer 210 comprises a fluid inlet 211, a fluid outlet 212, and a femoral component post 213. In some embodiments, the catheter 120 is in fluidic communication with the fluid inlet 211 of the knee spacer 210. In some embodiments, the negative pressure wound therapy pump 130 is in fluidic communication with the catheter 120 and the fluid outlet 212 of the knee spacer 210. In some embodiments, the location of the fluid inlet 211 is specified to be closer to a standard incision location.

Figure 9A:
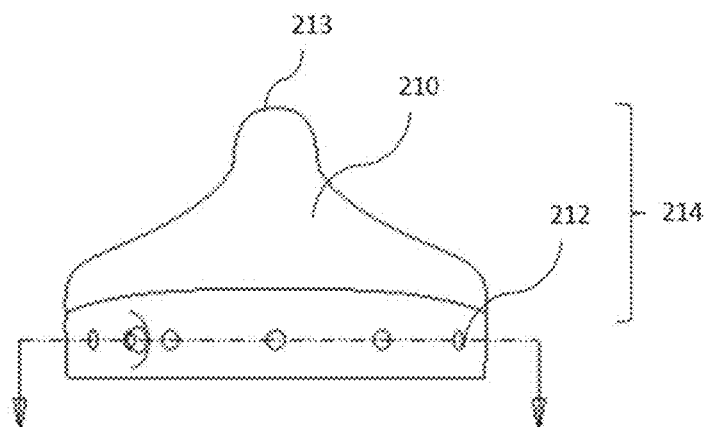
FIG. 9A shows a front-view illustration of an exemplary knee spacer, per an embodiment herein.
Figure 9B:
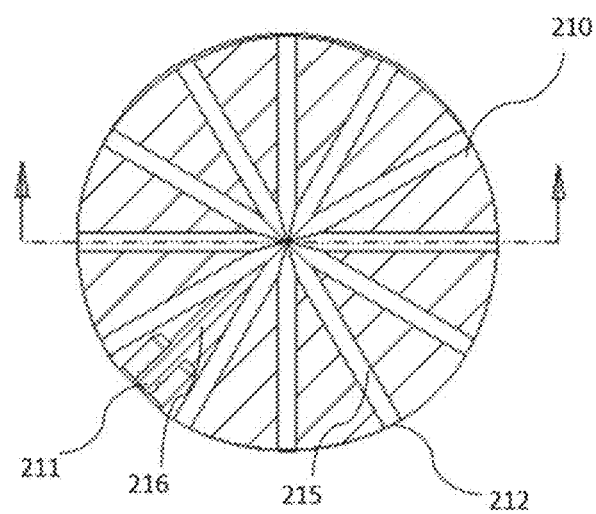
FIG. 9B shows a bottom cross-sectioned view illustration of an exemplary knee spacer, per an embodiment herein.
Figure 9C:
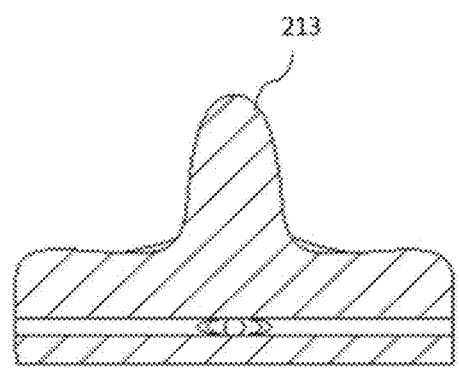
FIG. 9C shows a front cross-sectioned view illustration of an exemplary knee spacer, per an embodiment herein.

As shown in FIGS. 9A-9C, the knee spacer 210 comprises a plurality of fluid outlets 212 arranged in a polar array arranged about a center of the knee spacer 210. In some embodiments, the knee spacer 210 comprises 2, 4, 6, 8, 10, 12, 14, 16, 18, 20, 22, 24 or more fluid outlets 212. Further, as shown, in some embodiments, the fluid inlet 211 is arranged between two consecutive fluid outlets 212. Alternatively, in some embodiments, the fluid outlets 212 are arranged in a rectilinear array. In some embodiments, an inner diameter of the fluid inlet 211 is equal to an inner diameter of the fluid outlet(s) 212. In some embodiments, an inner diameter of the fluid inlet 211 is greater than an inner diameter of the fluid outlet(s) 212. In some embodiments, an inner diameter of the fluid inlet 211 is less an inner diameter of the fluid outlet(s) 212. In some embodiments, as shown in FIG. 9B, the fluid inlet 211 is in fluidic communication with the fluid outlets 212 via an inlet channel 216 and one or more outlet channels 215. In some embodiments, each outlet channel 215 corresponds to a fluid outlet 212. In some embodiments, one or more outlet channels 215 each correspond to one or more fluid outlets 212. In some embodiments, the inlet channel 216 and each of the outlet channels 215 intersect. In some embodiments, the inlet channel 216 and each of the outlet channels 215 intersect at a center axis of the knee spacer 210.

Figure 10A:
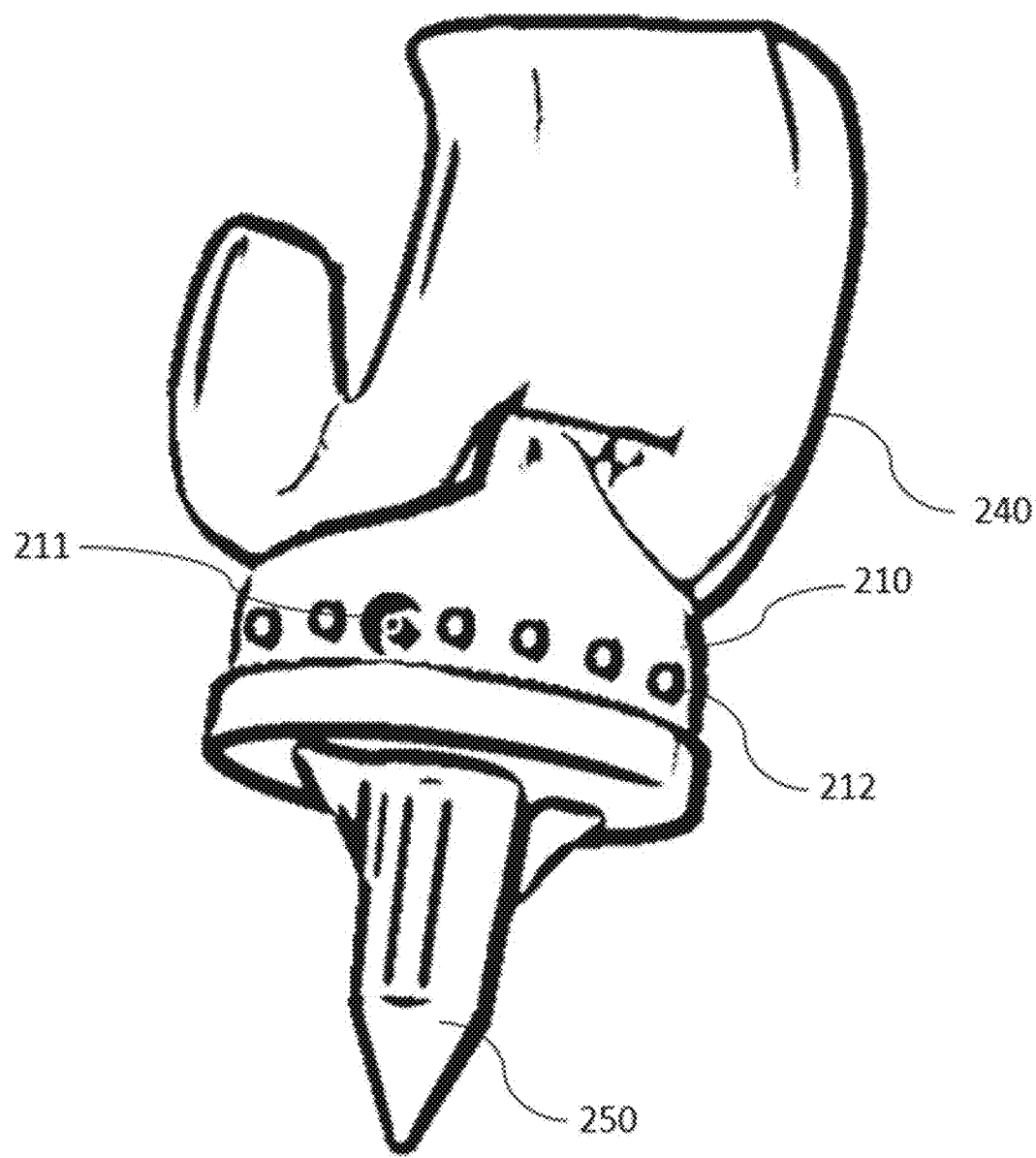
FIG. 10A shows a front-view illustration of an exemplary knee spacer disposed between a femoral implant and a tibial implant.

In some embodiments, per FIG. 10, the knee spacer 210 mates with a femoral component 240 and a tibial tray 250. In some embodiments, a femoral component post 213 of the knee spacer 210 mates with the femoral component 240. In some embodiments, the knee spacer 210 articulates about the retained femoral component 240. As shown, in some embodiments, the femoral component post 213 is symmetric about a plane. Further as shown in FIG. 9A, in some embodiments, a first surface 214 of the femoral component post 213 has a rounded outer edge. In some embodiments, the first surface 214 of the femoral component post 213 comprises a single uninterrupted surface. Further as shown, the knee spacer 210 comprises a single uniform body. Alternatively, in some embodiments, the knee spacer 210 comprises two or more bodies that are removably coupled.

In some embodiments, the catheter is removably coupled to the fluid inlet 211 of the knee spacer 210. In some embodiments, the fluid inlet 211 of the knee spacer 210 comprises a luer taper, a barb fitting, or both to removably couple to the catheter. In some embodiments, the fluid inlet 211 of the knee spacer 210 is configured to couple to the catheter intra-operatively. In some embodiments, the catheter is permanently coupled to the fluid inlet 211 of the knee spacer 210. In some embodiments, the knee spacer system 200A further comprises a sterile packaging enclosing the knee spacer 210. In some embodiments, the sterile packaging comprises a double sterile barrier for introduction into the sterile field.

In some embodiments, the knee spacer platform 200 is configured to be implanted during a short-period of time. In some embodiments, the knee spacer 210 provides local irrigation, drug administration, or both. In some embodiments, the fluid inlet 211 and the fluid outlet(s) 212 of the knee spacer 210 provide local irrigation, drug administration, or both. In some embodiments, the knee spacer 210 is made of a biocompatible polymer. In some embodiments, the biocompatible polymer is a synthetic polymer. In some embodiments, the synthetic polymer is low-density polyethylene (LDPE), high-density polyethylene (HDPE), polypropylene (PP), polyvinyl chloride (PVC) polystyrene (PS) nylon, polytetrafluoroethylene, or a thermoplastic polyurethane (TPU). In some cases, a biocompatible polymer is acetyl copolymer (e.g. Delrin® or Celcon®), silicone, polyether ether ketone (PEEK), a polyurethane, including a flexible polyurethane, a biocompatible elastomer, or a ultra-high molecular weight polyethylene (UHMWPE). In some embodiments, the knee spacer 210 is at least partially rigid. In some embodiments, the knee spacer 210 is at least partially flexible. In some embodiments, at least a portion of the knee spacer 210 has a modulus of elasticity of about 1 GPa to about 300 GPa.

In some embodiments, the knee spacer is configured to be positioned between the tibial and femoral components of a permanent knee prosthesis. The knee spacer has an additional function of protecting the surfaces of the prosthetic components during irrigation or treatment.

Figure 10B:
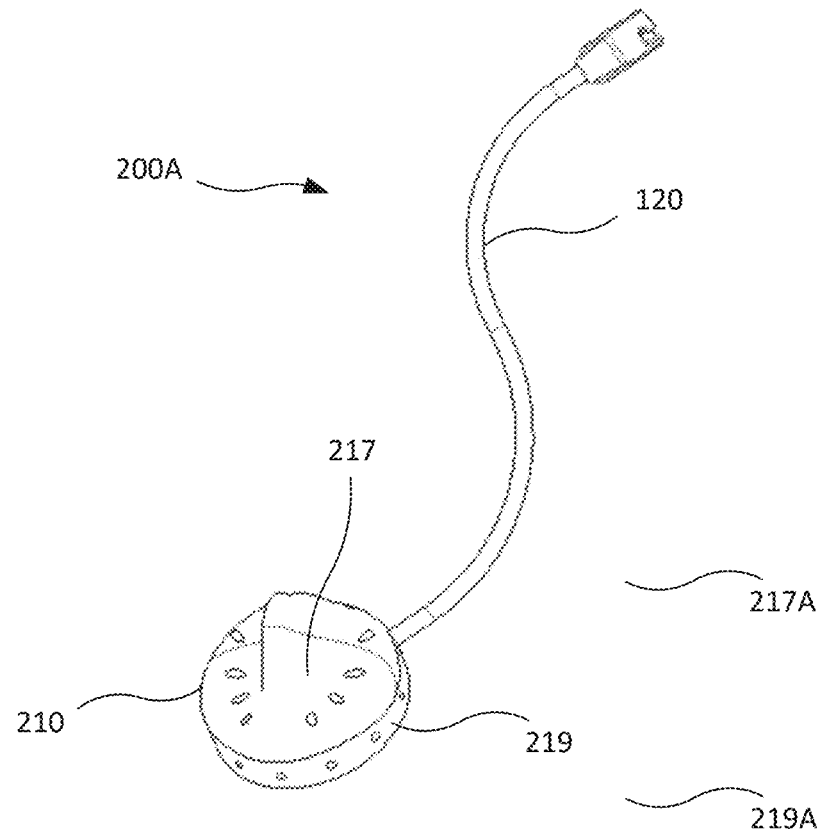
FIGS. 10B and 10C depict aspects of exemplary knee spacer systems, according to embodiments of the present invention.
Figure 10C:
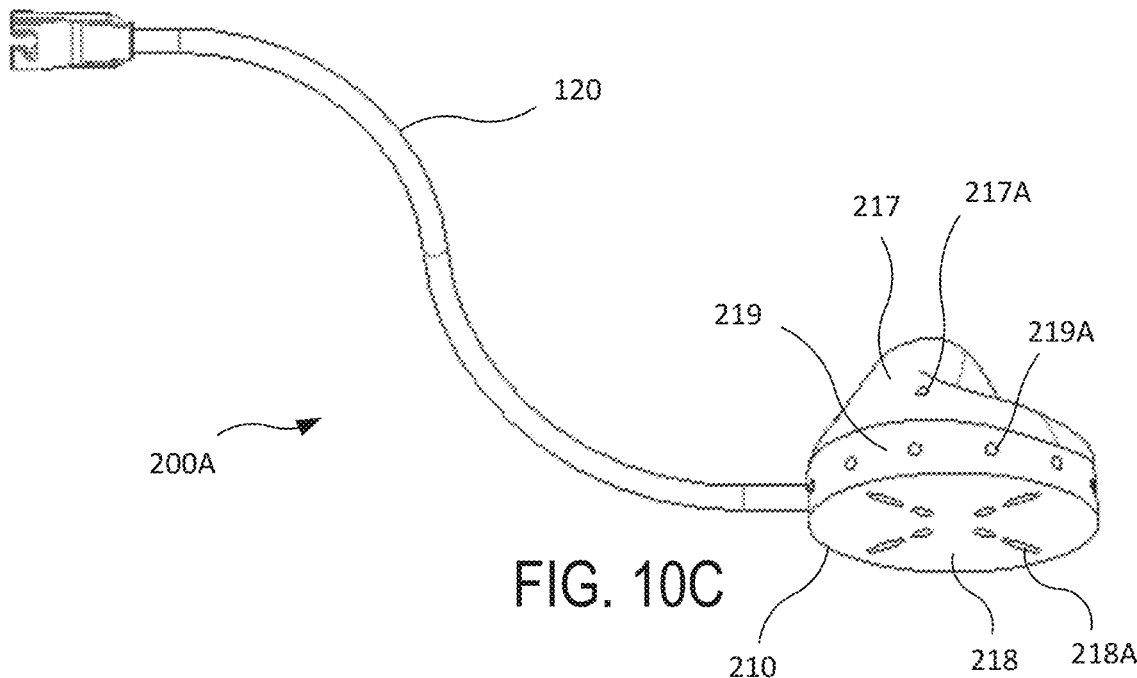

As shown in FIGS. 10B and 10C, a knee spacer system 200A can include a knee spacer 210 and a catheter 120. The knee spacer 210 can be coupled with a retained femoral component and tibial component of a permanent knee prosthesis. In some cases, the femoral component can include one or more fluid outlets or apertures whereby fluid provided via the spacer 210 can flow therethrough and toward femoral bone. In some cases, the tibial component can include one or more fluid outlets or apertures whereby fluid provided via the spacer 210 can flow therethrough and toward tibial bone. Spacer 210 includes a first surface 217 configured for articulating engagement with a first implant (e.g. femoral implant), a second surface 218 configured for fixed engagement with a second implant (e.g. tibial implant), and an exposed surface 219 disposed between the first surface 217 and the second surface 218. A knee spacer 210 can include outlets through which treatment fluid may flow. For example, first surface 217 can include outlets 217A through which treatment fluid may flow toward a femoral implant, second surface 218 can include outlets 218A through which treatment fluid may flow toward a tibial implant, and exposed surface 219 can include outlets 219A through which treatment fluid may flow into a joint space between the femoral implant and the tibial implant, for example to treat the nearby soft tissue.

Shoulder Spacer Platforms, Systems, and Devices

Figure 11:
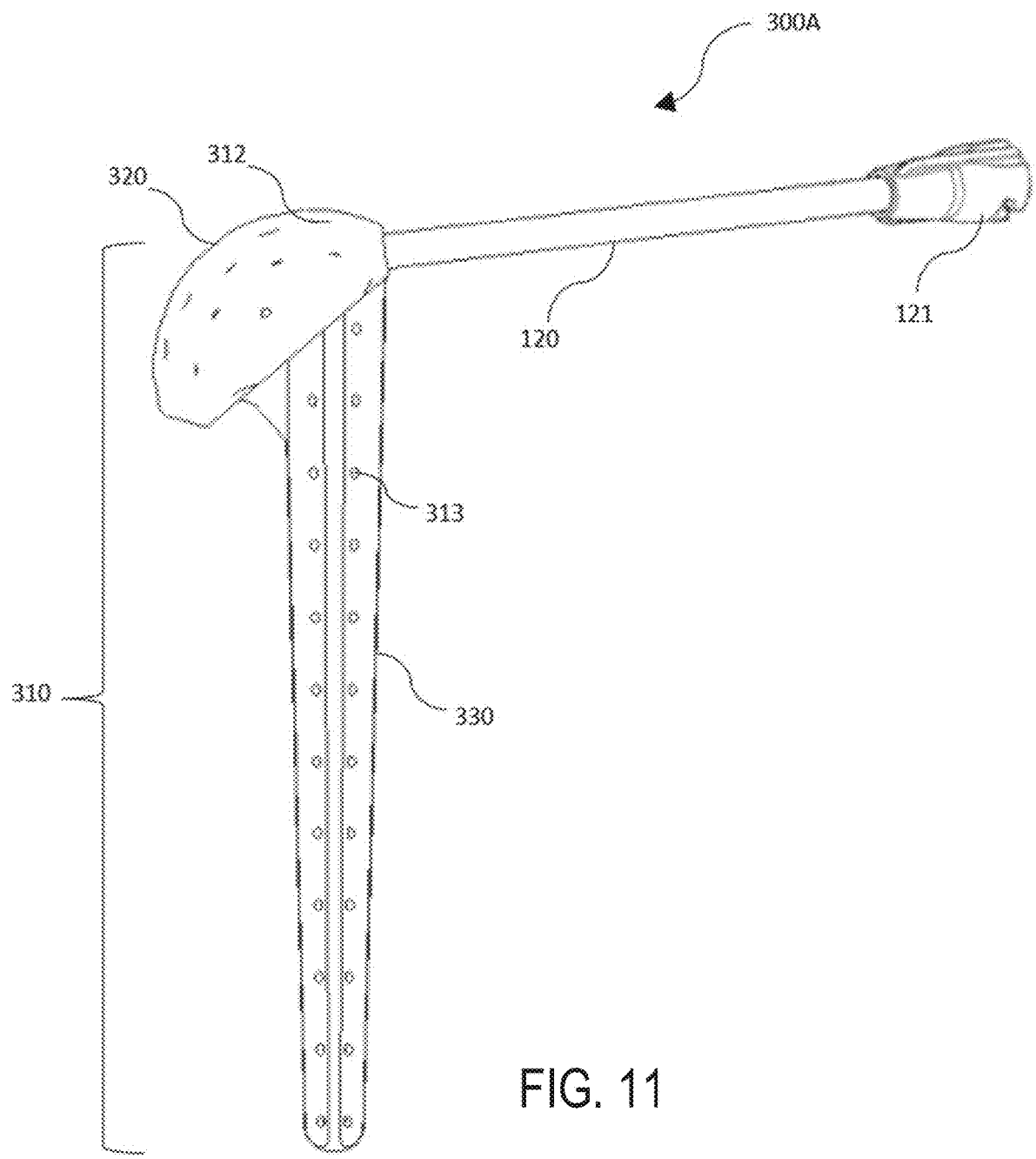
FIG. 11 shows a front-top perspective illustration of an exemplary shoulder spacer system, per an embodiment herein.

Provided herein, is a shoulder spacer platform comprising a shoulder spacer system (e.g. 300A or 300B) and a negative pressure wound therapy pump as described herein 130. It is understood that the instant disclosure is not limited to a NPWT pump, and that any infusion and vacuum pump may be used. For example, embodiments encompass shoulder spacer platforms which include a vacuum pump with gravity infusion. In some embodiments, per FIG. 11, the shoulder spacer system 300A comprises a shoulder spacer 310 and a catheter 120. In contrast to other embodiments disclosed herein involving an interpositional spacer (e.g. for placement between two implanted prosthetic components) such as hip spacer 110 shown in FIG. 3A, knee spacer 210 shown in FIG. 8B, and shoulder spacer 350 shown in FIG. 13A, it can be seen that shoulder spacer 310 of FIG. 11 would not be placed between two implanted prosthetics (e.g. between a humeral stem and a glenoid component of a shoulder prosthesis), because shoulder spacer 310 includes humeral stem 330. In some embodiments, the humeral head 320 is removably coupled to the humeral stem 330. In some embodiments, the humeral head 320 is coupled to the humeral stem 330 via a tapered connection, a dovetail connection, a threaded connection, a flanged connection, a snap buckle, a winged nut, or any other coupling mechanism. In some embodiments, the coupling mechanism allows for offset adjustments. Such embodiments allow for reduced inventory and better patient matching. According to some embodiments, shoulder spacer 310 depicted in FIG. 11 can be used to replace a permanent shoulder prosthetic implant. According to some embodiments, shoulder spacer 310 depicted in FIGS. 12A to 12C can be used to replace a permanent shoulder prosthetic implant. In some cases, shoulder spacer 310 can be used in conjunction with a permanent glenoid prosthetic implant, such as implant 60 depicted in FIG. 14D.

It is appreciated that shoulder spacer 310 or shoulder spacer system 300A can include any one or more features of the devices or can be configured to perform any one or more of the treatment method aspects of those disclosed in U.S. Provisional Patent Application Nos. 61/208,540 filed Feb. 25, 2009 or 62/180,986 filed Jun. 17, 2015, or in U.S. Patent Publication Nos. 2010/0217401 or 2016/0367371. The content of each of these filings is incorporated herein by reference.

Figures 12A, 12B, 12C:
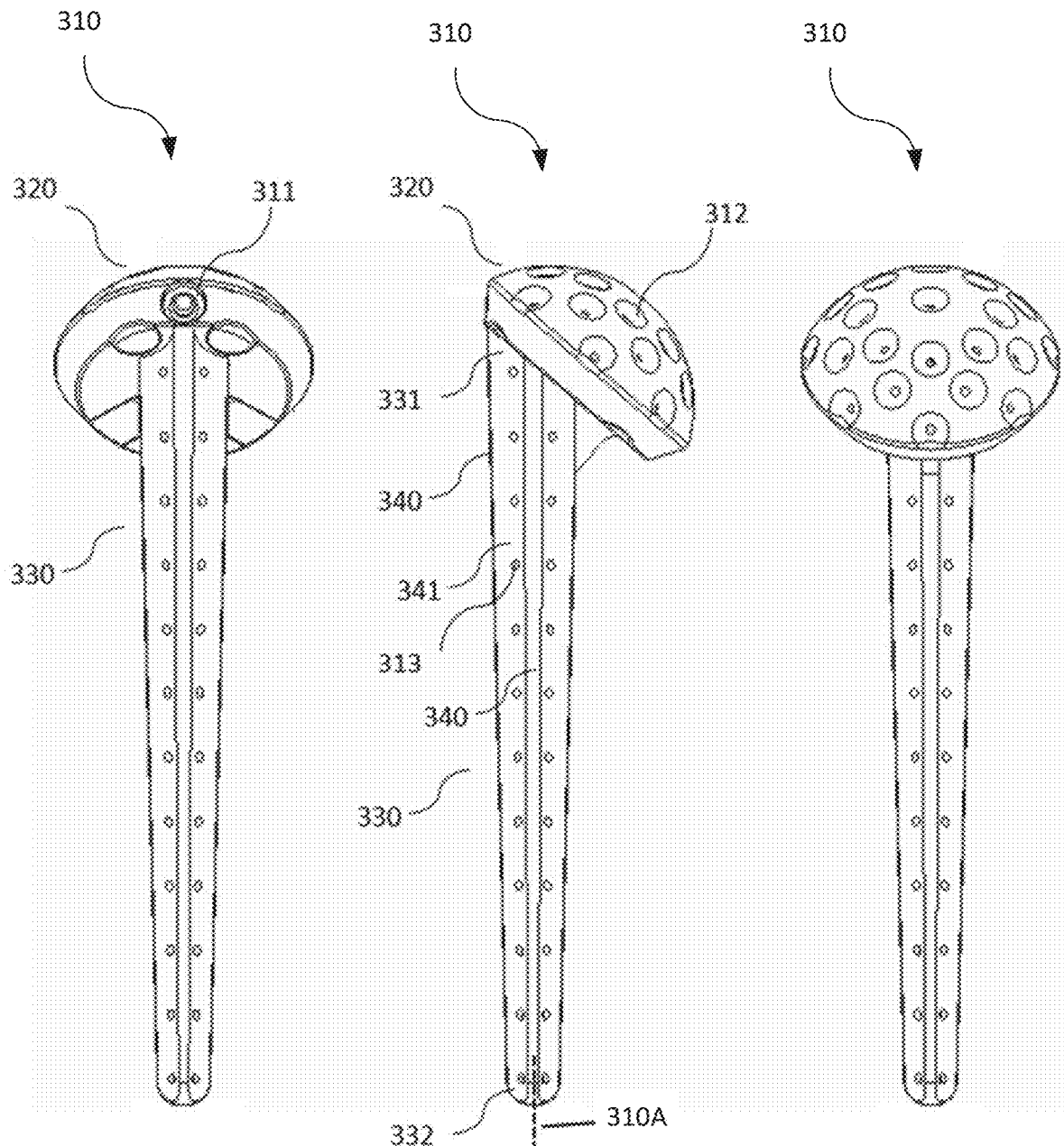
FIG. 12A shows a back-view illustration of an exemplary shoulder spacer, per an embodiment herein.
FIG. 12B shows a left-view illustration of an exemplary shoulder spacer, per an embodiment herein.
FIG. 12C shows a front-view illustration of an exemplary shoulder spacer, per an embodiment herein.
Figure 13A:
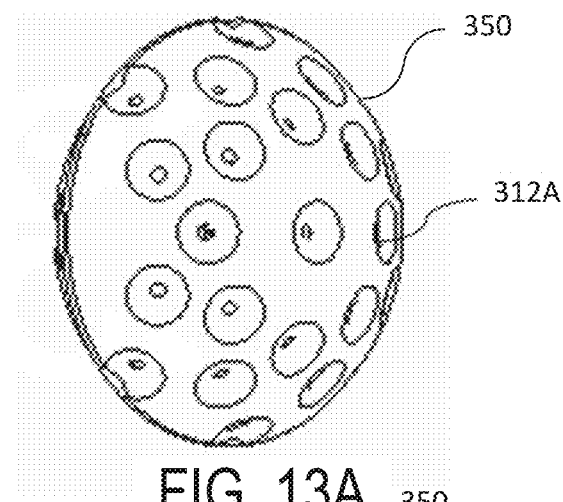
FIG. 13A shows a top-left perspective view illustration of a humeral head of an exemplary shoulder spacer, per an embodiment herein.
Figure 13B:
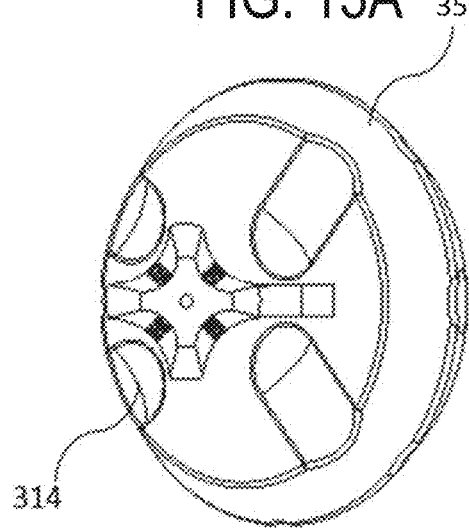
FIG. 13B shows a bottom-right perspective view illustration of a humeral head of an exemplary shoulder spacer, per an embodiment herein.
Figure 13C:
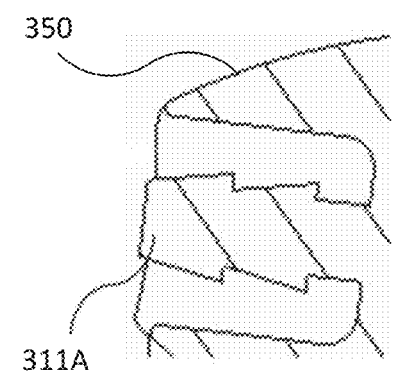
FIG. 13C shows a detailed left cross-sectioned view illustration of an inlet of a humeral head of an exemplary shoulder spacer, per an embodiment herein.

In some embodiments, the shoulder spacer 310 comprises a fluid inlet 311 as shown in FIG. 12A. Likewise, a shoulder spacer 350 as shown in FIG. 13C can include a fluid inlet 311A. In some embodiments, the shoulder spacer 310 comprises one or more head fluid outlets 312. Likewise, a shoulder spacer 350 as shown in FIG. 13B can include one or more fluid outlets 312A. In some embodiments, the catheter 120 is in fluidic communication with the fluid inlet 311 of the shoulder spacer 310 (or with inlet 311A of shoulder spacer 350). In some embodiments, the negative pressure wound therapy pump 130 is in fluidic communication with the catheter 120, and the fluid outlet(s) 313. In some embodiments, the catheter 120 is coupled to the NPWT pump via a connection 121. In some embodiments, the location of the fluid inlet 311 (or 311A) is specified to be closer to a standard incision location. Also provided herein is a shoulder spacing kit comprising two or more sizes of the shoulder spacer system and the negative pressure wound therapy pump (or any infusion and vacuum pump), so as to accommodate various patient anatomies. Hence, in some cases, a shoulder spacer platform or shoulder spacing kit may or may not include a NPWT pump.

As shown in FIGS. 12A-13C, a humeral head or surface (e.g. of a shoulder spacer 310 depicted in FIGS. 11-12C or an interpositional shoulder spacer 350 depicted in FIGS. 12D-13B) can include a plurality of fluid outlets 312 or 312A, respectively, arranged in a polar array about a center of the humeral head 320 or spacer 350, respectively. In some embodiments, the humeral head 320 or shoulder spacer 350 comprises 2, 4, 6, 8, 10, 12, 14, 16, 18, 20, 22, 24 or more fluid outlets 312 or 312A, respectively. Alternatively, in some embodiments, the fluid outlets 312 or 312A are arranged in a rectilinear array. In some embodiments, an inner diameter of the fluid inlet 311 or 311A is equal to an inner diameter of the fluid outlet(s) 312 or 312A, respectively. In some embodiments, an inner diameter of the fluid inlet 311 or 311A is greater than an inner diameter of the fluid outlet(s) 312 or 312A, respectively. In some embodiments, an inner diameter of the fluid inlet 311 or 311A is less than an inner diameter of the fluid outlet 312(s) or 312A(s), respectively. In some embodiments, the fluid inlet 311 or 311A is in fluidic communication with the fluid outlets 312 or 312A, respectively, via an inlet channel and one or more outlet channels. In some embodiments, each outlet channel corresponds to a fluid outlet 312 or 312A. In some embodiments, one or more outlet channels each correspond to one or more fluid outlets 312 or 312A. In some embodiments, the inlet channel and each of the outlet channels intersect. In some embodiments, the inlet channel and each of the outlet channels intersect at a center axis of the shoulder spacer 310 (or stem thereof) or shoulder spacer 350.

In some embodiments, an interpositional shoulder spacer 350 comprises one or more fluted channels 314 as depicted in FIG. 13B. In some embodiments, the one or more fluted channels 314 are arrayed about a center axis of the shoulder spacer 350. In some embodiments, the shoulder spacer 350 comprises 1, 2, 3, 4, 5, 6, 7, 8, 9, 10, or more fluted channels 314 arrayed about the shoulder spacer 350. In some embodiments, one of more of the fluted channels 314 may include one or more fluid outlets. In some embodiments, the fluted channels 314 enable fluid flow under the shoulder spacer 350, between the shoulder spacer 350 and the humeral stem. In some embodiments, the shoulder spacer 350 is undersized to allow fluid flow thereover. It is understood that shoulder spacer 310 may include one or more similar fluted channels having one or more properties of the fluted channels 314 described here. It is also understood that hip spacer 110 and knee spacer 210 may include one or more similar fluted channels having one or more properties of the fluted channels 314 described here.

As shown in FIGS. 12A-C, in some embodiments, the humeral stem 330 comprises an elongate body having a longitudinal axis 310A, wherein the humeral stem 330 comprises a first end 331 and a second end 332 opposite the first end. The second, or distal, end 332 may be disposed in the medullary canal of a bone. In some embodiments, the humeral stem 330 can vary in size and/or longitudinal length. In some embodiments, the humeral stem 330 comprises a stem channel extending between the first end 331 and the second end 332. In some embodiments, the stem channel is configured to deliver fluid to the medullary canal via the one or more stem fluid outlets 313.

In some embodiments, the humeral stem 330 comprises a plurality of protrusions 340, protruding radially outward from a center axis of the humeral stem 330. The plurality of protrusions 340 may comprise any number of protrusions having any appropriate shape, size, or configuration to engage the medullary canal in a stable fashion. For example, the protrusions may comprise elongate fins extending along the longitudinal length of the humeral stem 330. In one exemplary embodiment, the plurality of protrusions 340 may comprise four fins, spaced equally at about 90° about the longitudinal axis 310A of the humeral stem 330. The plurality of protrusions 340 and the humeral stem 330 may be formed separately and coupled together. Alternatively or in combination, the plurality of protrusions 340 may be formed by removing material from the humeral stem 330, such that the plurality of protrusions and the humeral stem 330 are formed as a single member. Adjacent protrusions 340 may define one or more fluted regions 341 therebetween, wherein the fluted regions 341 are radially recessed compared to the protrusions 340. The fluted regions 341 may form a concave recessed region between adjacent protrusions 340.

The plurality of protrusions 340 and fluted regions 341 can be configured to minimize the surface area of the humeral stem 330 contacting the bone lining the medullary canal, such that the area of the bone flush with fluid being delivered via the fluid inlet 311 may be maximized. For example, the plurality of protrusions 340 and fluted regions 341 can be configured such that less than 50% of the surface area of the humeral stem 330 is in contact with the bone lining the medullary canal. Of course, this is not intended to be limiting and one of skill in the art will appreciate that any percentage of the surface area of the humeral stem 330 may contact the bone. In some embodiments, the humeral stem 330 comprises a plurality of identical fluted regions 341 defined by a plurality of elongate fins 340, distributed symmetrically about the longitudinal axis 310A of the humeral stem 330. Alternatively, a plurality of fluted regions 341 may be distributed asymmetrically about the longitudinal axis of the humeral stem 330, and/or may have different shapes or sizes.

In some embodiments, the humeral stem 330 comprises fluted regions 341 to allow for fluid flow in the medullary canal, allow for fluid flow between medullary canal and the joint space where a NPWT sponge will be.

In some embodiments, the plurality of stem fluid outlets 313 are in fluid communication with the internal channel of the humeral stem 330. The plurality of stem fluid outlets 313 may be configured to deliver the fluid, distributed through the humeral stem 330 internal channel, to the medullary canal, as well as adjacent tissue including the joint. The plurality of stem fluid outlets 313 may be disposed in one or more fluted regions 341, so as to deliver the fluid to the area of the bone not in contact with the humeral stem 330. The plurality of stem fluid outlets may comprise any number of outlet holes having any appropriate size, shape, or distribution. For example, the plurality of outlet holes may include a plurality of equally sized and spaced holes that extend axially along a line substantially parallel to the longitudinal axis 310A of the humeral stem 330. The plurality of outlet holes may be arranged in various configurations. The plurality of outlet holes may comprise holes having an identical shape and/or size, or holes having various shapes and/or sizes. Varying the hole size may allow further fluid control of the fluid as it exits different regions of the humeral stem 330.

The humeral stem 330 may be tapered to fit the medullary canal. For example, the humeral stem 330 and/or the plurality of protrusions 340 may be tapered from the first end 331 to the second end 332, as shown, so as to have a smaller radial cross-sectional area at the second end than at the first end. For example, the taper may comprise a gradual taper, wherein the extent of the taper may be preferably in a range from about 0.1° to about 10°, more preferably about 0.5° to about 5°, and even more preferably about 1° to about 5°, or about 1° to about 4°, or about 2° or about 3°. The taper may be adjusted to accommodate a medullary canal of a specific type of bone.

In some embodiments, the catheter is removably coupled to the fluid inlet 311 of the shoulder spacer 310. In some embodiments, the fluid inlet 311 of the shoulder spacer 310 comprises a luer taper, a barb fitting, or both to removably couple to the catheter. In some embodiments, the fluid inlet 311 of the shoulder spacer 310 is configured to couple to the catheter intra-operatively. In some embodiments, the catheter is permanently coupled to the fluid inlet 311 of the shoulder spacer 310. In some embodiments, the shoulder spacer system 300A further comprises a sterile packaging enclosing the shoulder spacer 310. In some embodiments, the sterile packaging comprises a double sterile barrier for introduction into the sterile field.

In some embodiments, the shoulder spacer platform is configured to be implanted during a short-period of time. In some embodiments, the shoulder spacer 310 provides local irrigation, drug administration, or both. In some embodiments, the fluid inlet 311 and the fluid outlet(s) 312 of the shoulder spacer 310 provide local irrigation, drug administration, or both. In some embodiments, the shoulder spacer 310 is made of a biocompatible polymer. In some embodiments, the biocompatible polymer is a synthetic polymer. In some embodiments, the synthetic polymer is low-density polyethylene (LDPE), high-density polyethylene (HDPE), polypropylene (PP), polyvinyl chloride (PVC) polystyrene (PS) nylon, polytetrafluoroethylene, or a thermoplastic polyurethane (TPU). In some cases, a biocompatible polymer is acetyl copolymer (e.g. Delrin® or Celcon®), silicone, polyether ether ketone (PEEK), a polyurethane, including a flexible polyurethane, a biocompatible elastomer, or a ultra-high molecular weight polyethylene (UHMWPE). In some embodiments, the shoulder spacer 310 or shoulder spacer 350 is at least partially rigid. In some embodiments, the shoulder spacer 310 or shoulder spacer 350 is at least partially flexible. In some embodiments, at least a portion of the shoulder spacer 310 or shoulder spacer 350 has a modulus of elasticity of about 1 GPa to about 300 GPa.

In some embodiments, the shoulder spacing kit comprises two or more sizes of the shoulder spacer 310, two or more sizes of the humeral stem 330, or both. In some embodiments, the shoulder spacing kit comprises two or more sizes of the shoulder spacer 350.

In some embodiments, the shoulder spacer 350 is configured to be positioned between the humeral stem and glenoid components of a permanent shoulder prosthesis. The shoulder spacer has an additional function of protecting the surfaces of the prosthetic components during an irrigation or treatment period. In some embodiments, the shoulder spacer 310 is configured to be positioned adjacent a glenoid component of a permanent shoulder prosthesis.

Figure 12D:
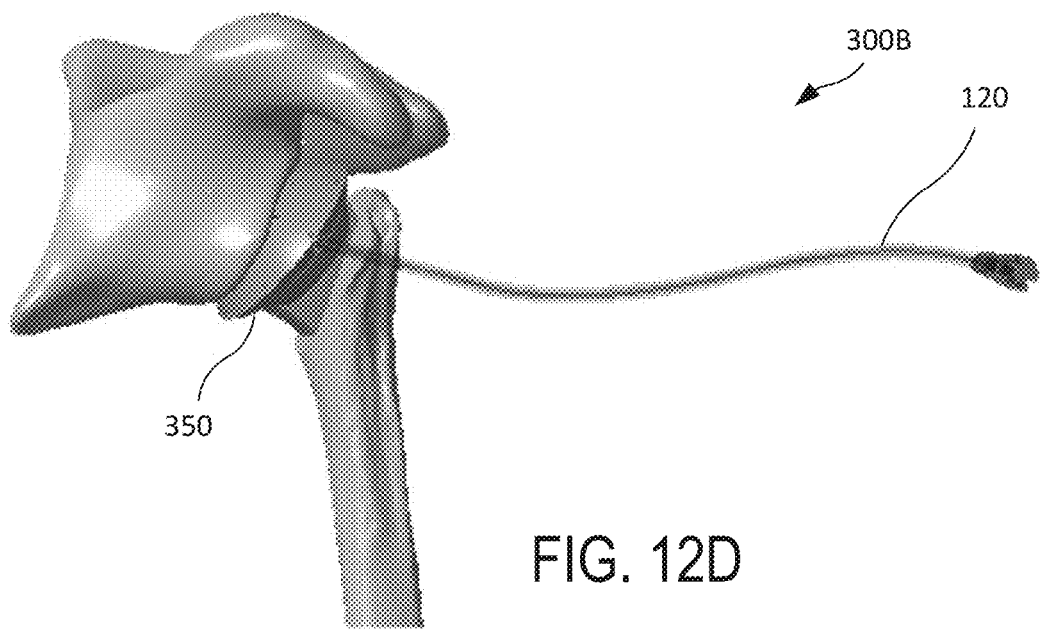
FIGS. 12D and 12E depict aspects of exemplary shoulder spacer systems, according to embodiments of the present invention.
Figure 12E:
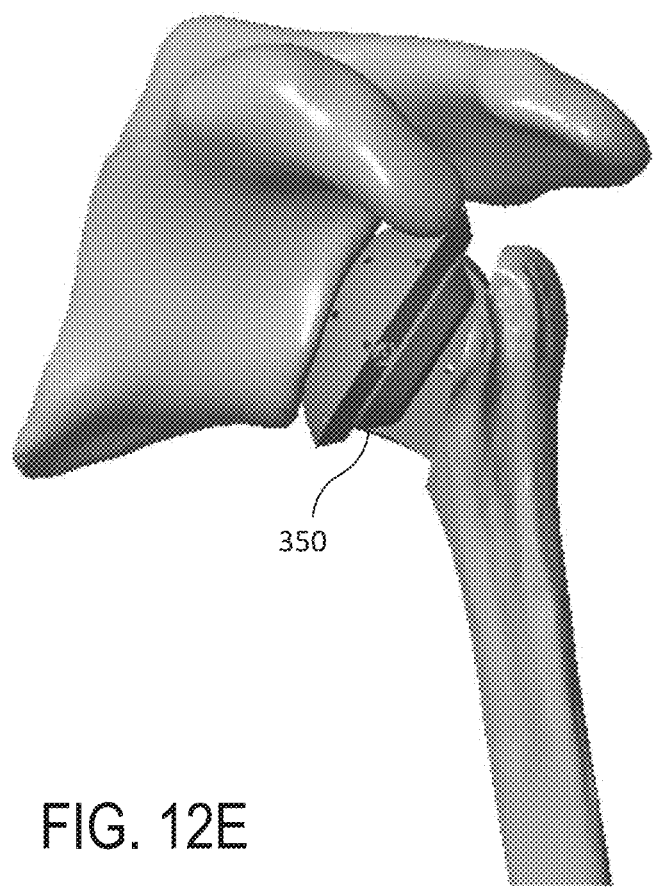

FIG. 12D depicts shoulder spacer system 300A engaged with a glenoid bone and a humerus bone of a patient. Shoulder spacer system 300A includes a shoulder spacer 310 and a catheter 120. Similarly, FIG. 12E depicts shoulder spacer 350 engaged with a glenoid bone and a humerus bone of a patient.

Figure 14A:
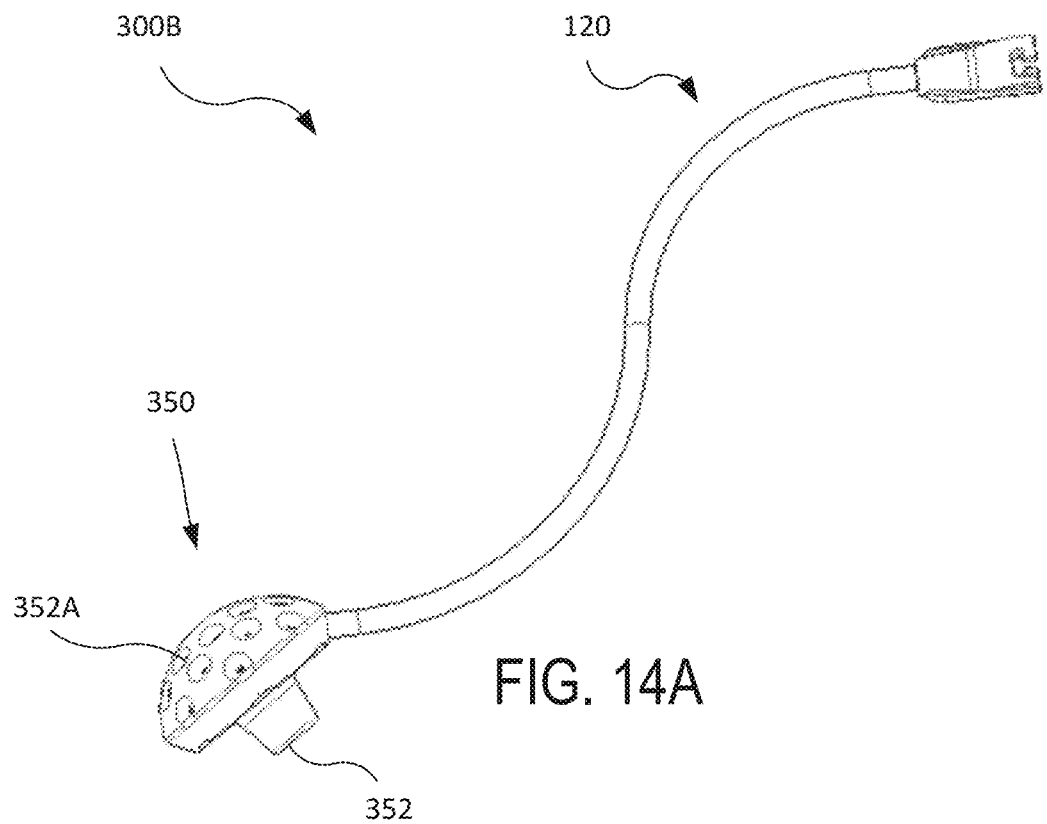
FIGS. 14A to 14D depict aspects of exemplary shoulder spacer systems, according to embodiments of the present invention.
Figure 14B:
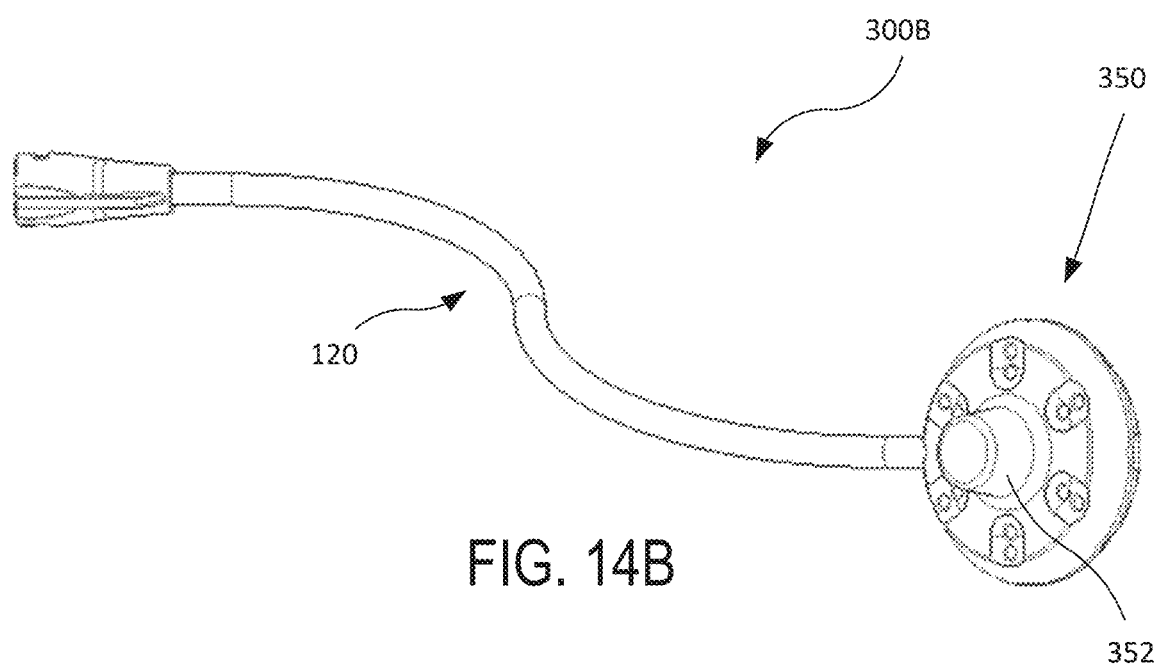
Figure 14C:
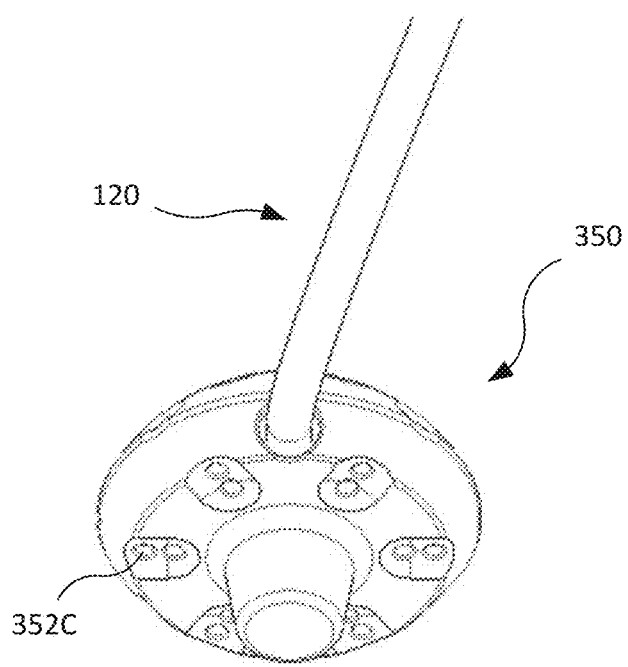
Figure 14D:
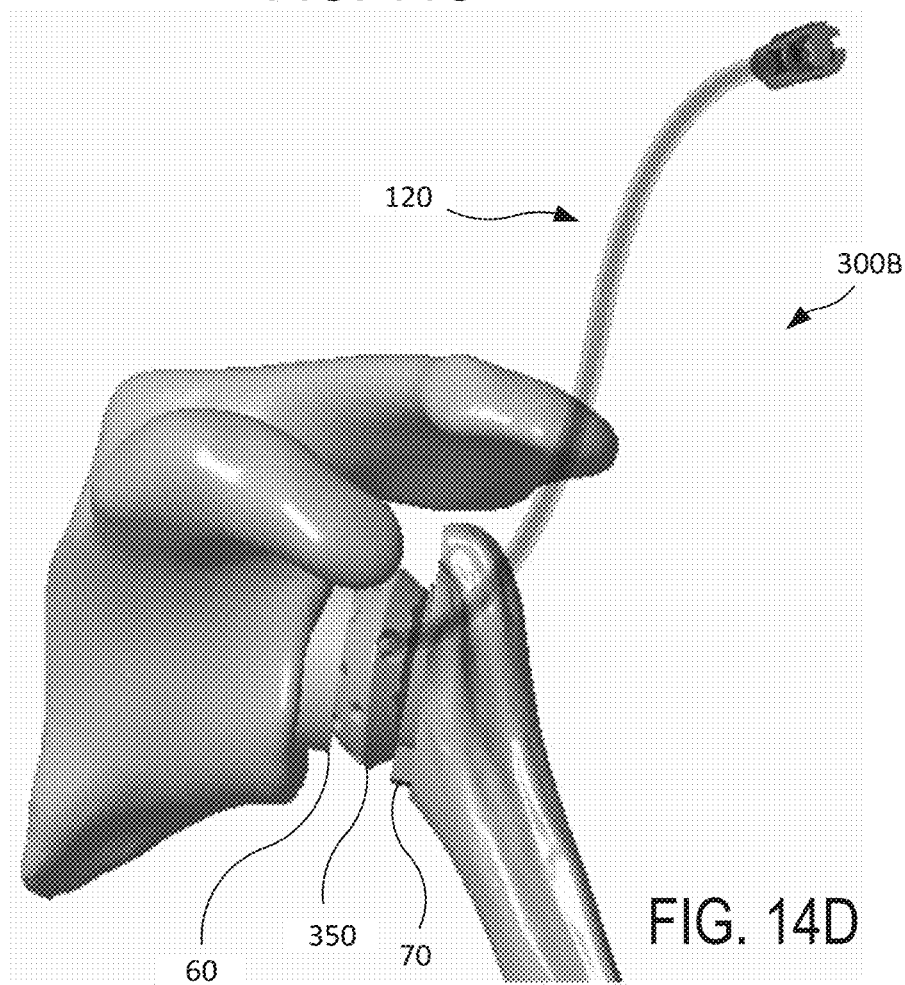

In some embodiments, per FIGS. 14A-14D, the shoulder spacer system 300B comprises a shoulder spacer 350 and a catheter 120. It can be seen that shoulder spacer 350 includes a protrusion 352 which can engage a permanent prosthetic component, such as a humeral stem prosthetic component. A shoulder spacer 350 can be placed between a glenoid implant and a humeral implant of a permanent prosthesis. Fluid outlets may be positioned all over the shoulder spacer. For example, fluid outlets 352A may be on the spacer surface that contacts the glenoid implant prosthetic component. In this way, antibiotic or other materials can be provided into the glenoid implant 60, which itself may have holes in it, so as to facilitate the flow or delivery of antibiotic or other materials to glenoid bone. Fluid outlets may be on the exposed surface of the spacer 350. Such outlets can facilitate the flow of treatment fluid to joint space between the first and second implants. Shoulder spacer 350 can also include outlets 352C which facilitate the flow of treatment fluid to spaces between the spacer and the second implant (e.g. humeral stem 70), and such flow may also be facilitated by the presence of fluted channels on the underside of the spacer. In the embodiment depicted in FIG. 14D, the shoulder spacer 350 can be used in a situation where the original prosthetic (e.g. glenoid component 60) included a metal cup or shell which is attached with the glenoid bone, a liner (e.g. plastic) which is disposed within the metal cup or shell, a spherical head which articulates against or otherwise engages the liner, and stem or trunnion which is coupled with the spherical head or ball, and the surgical procedure involves removing the liner and spherical head, and temporarily inserting therefore the shoulder spacer 350 (e.g. while retaining the cup/shell of the glenoid component 60). In contrast, the shoulder spacer 350 depicted in FIG. 12D can be used when the stem and spherical head of the original prosthetic are retained, and only the liner or liner and cup are removed. The shoulder spacer 350 of FIGS. 12D and 14D may be the same, where shoulder spacer 350 of FIG. 12D is used when the glenoid prosthetic component is removed, and shoulder spacer 350 of FIG. 14D is used when the glenoid prosthetic component 60 is retained. In some cases, a shoulder spacer can be used when a spherical head of the humeral prosthetic implant is retained. In some cases, a shoulder spacer can be used when a spherical head of the humeral prosthetic implant is removed.

Figure 15:
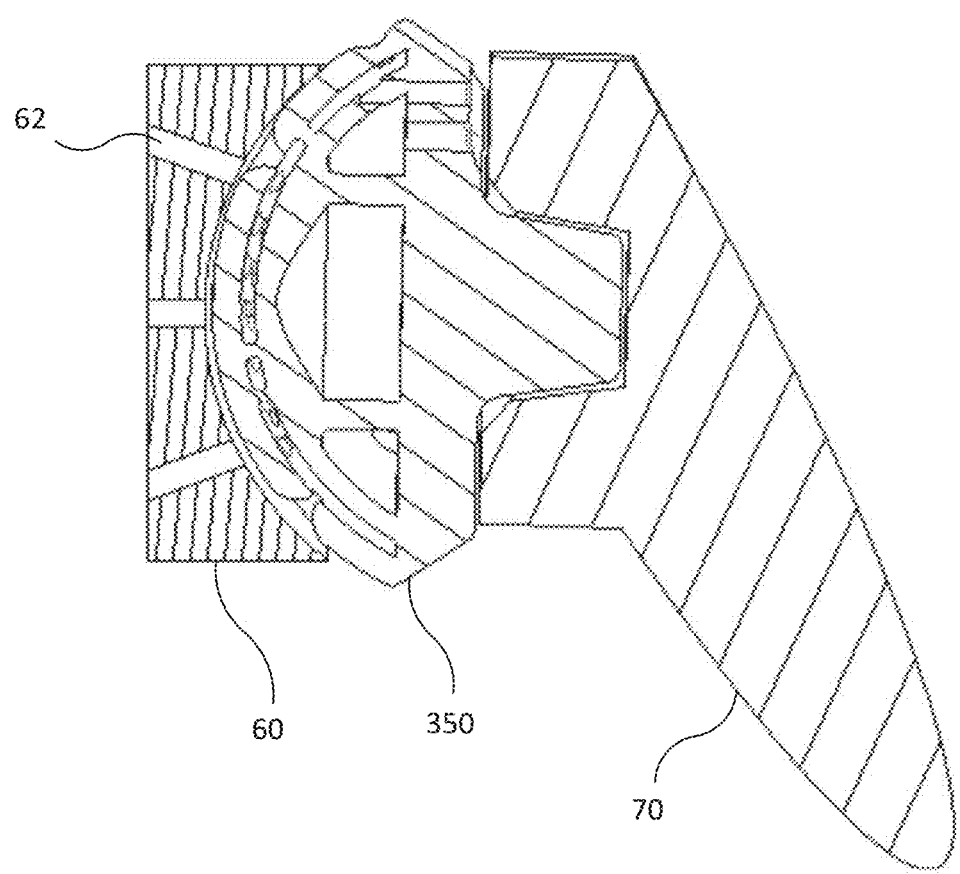
FIG. 15 depicts aspects of exemplary shoulder spacer systems, according to embodiments of the present invention.

FIG. 15 depicts aspects of a shoulder spacer 350 according to embodiments of the present invention. As shown here, shoulder spacer 350 can be engaged with a glenoid implant component 60 and a humeral implant component 70 of a previously implanted prosthesis. As shown here, glenoid component 60 includes one or more holes or apertures 62 whereby fluid provided via the spacer 350 can flow therethrough and toward glenoid bone.

Figure 16A:
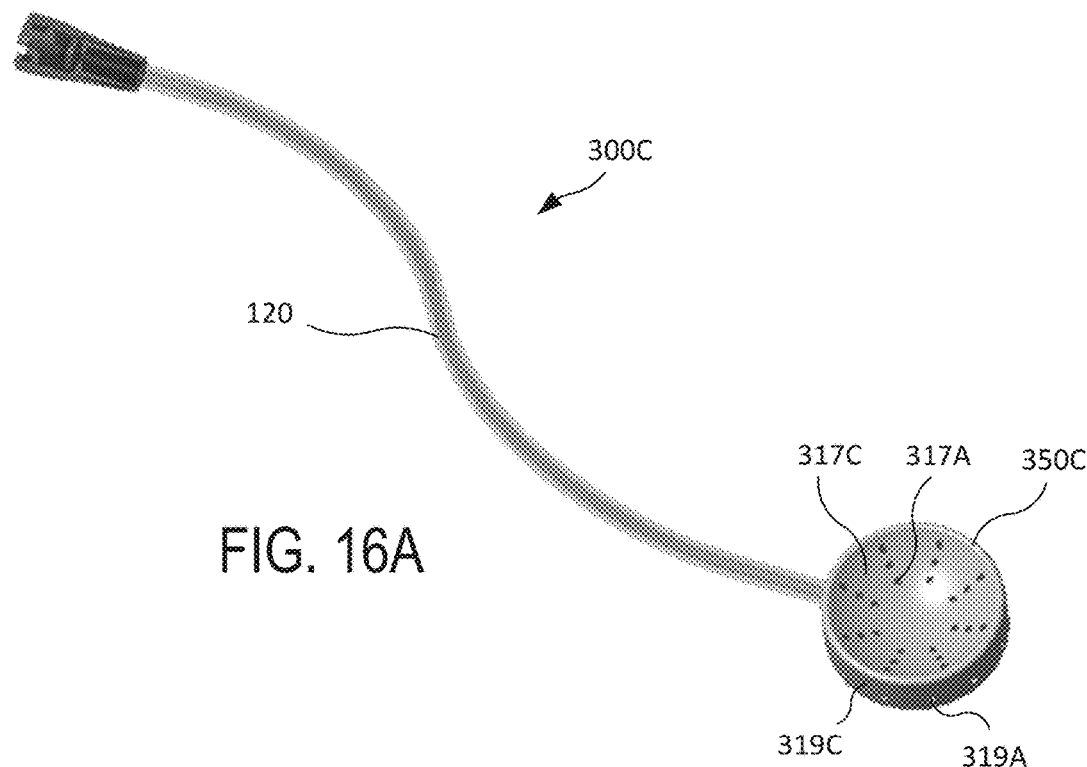
FIGS. 16A and 16B illustrate aspects of exemplary reverse shoulder spacer systems, according to embodiments of the present invention.
Figure 16B:
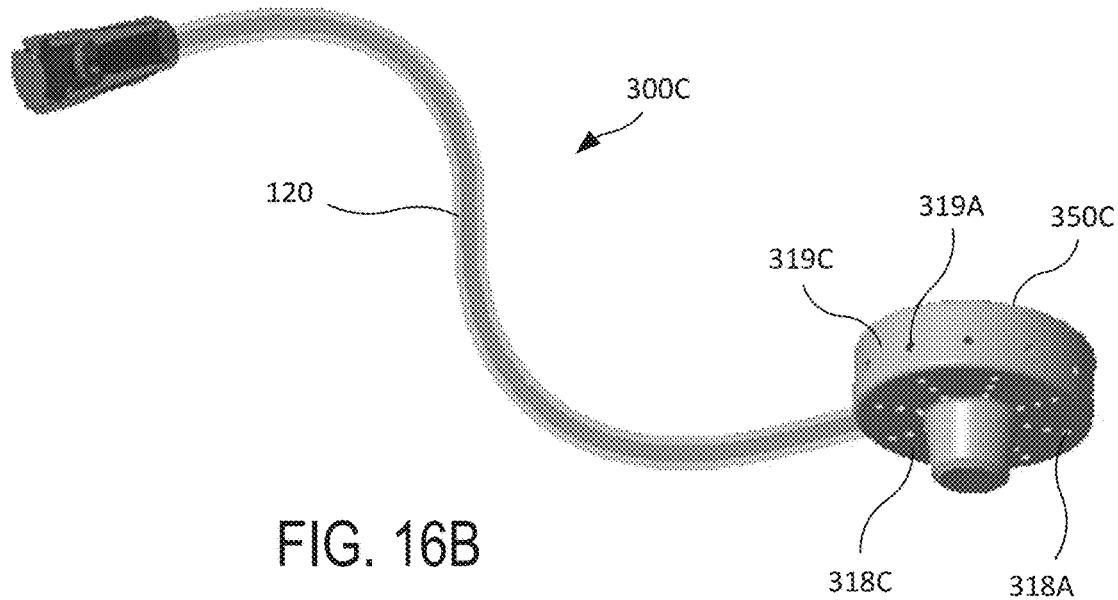

In addition to the anatomical shoulder spacer embodiments discussed above, embodiments of the present invention also encompass reverse shoulder spacer embodiments. For example, FIGS. 16A and 16B illustrate aspects of an exemplary reverse shoulder spacer system 300C. As depicted here, reverse shoulder spacer system 300C includes a reverse shoulder spacer 350C and a catheter 120. Reverse shoulder spacer 350C includes a first surface 317C configured for articulating engagement with a first implant (e.g. glenoid implant), a second surface 318C configured for fixed engagement with a second implant (e.g. humeral implant), and an exposed surface 319C disposed between the first surface 317C and the second surface 318C. A reverse shoulder spacer 350C can include outlets through which treatment fluid may flow. For example, first surface 317C can include outlets 317A through which treatment fluid may flow toward a glenoid implant, second surface 318C can include outlets 318A through which treatment fluid may flow toward a humeral implant, and exposed surface 319C can include outlets 319A through which treatment fluid may flow into a joint space between the glenoid implant and the humeral implant, for example to treat the nearby soft tissue.

Figure 17A:
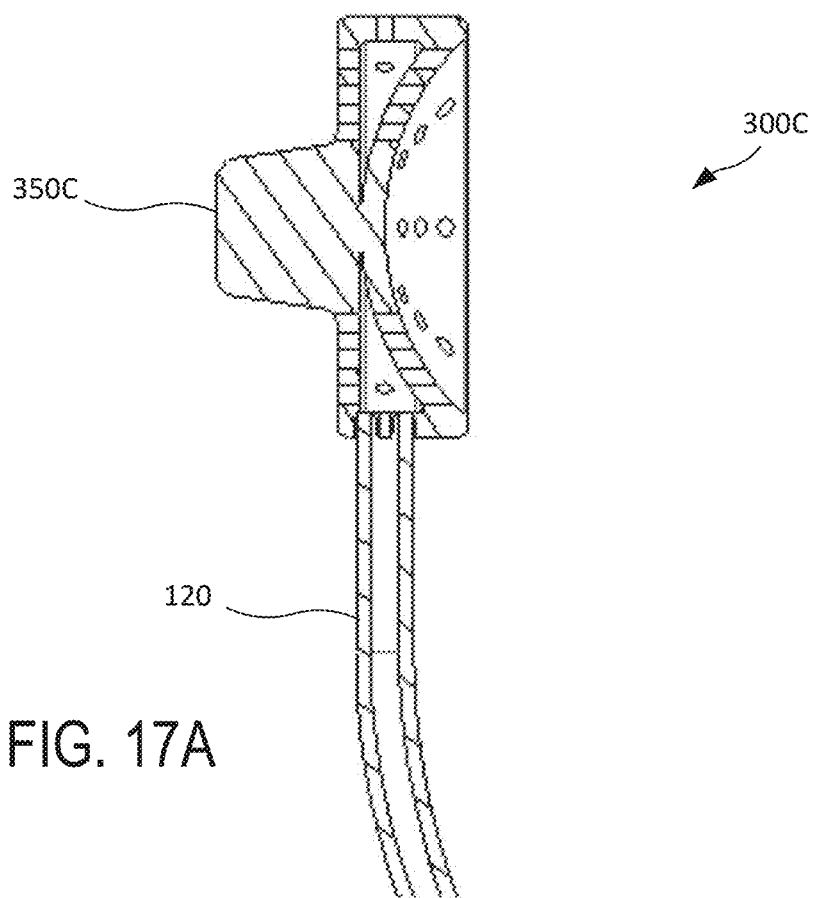
FIGS. 17A and 17B illustrate aspects of exemplary reverse shoulder spacer systems, according to embodiments of the present invention.
Figure 17B:
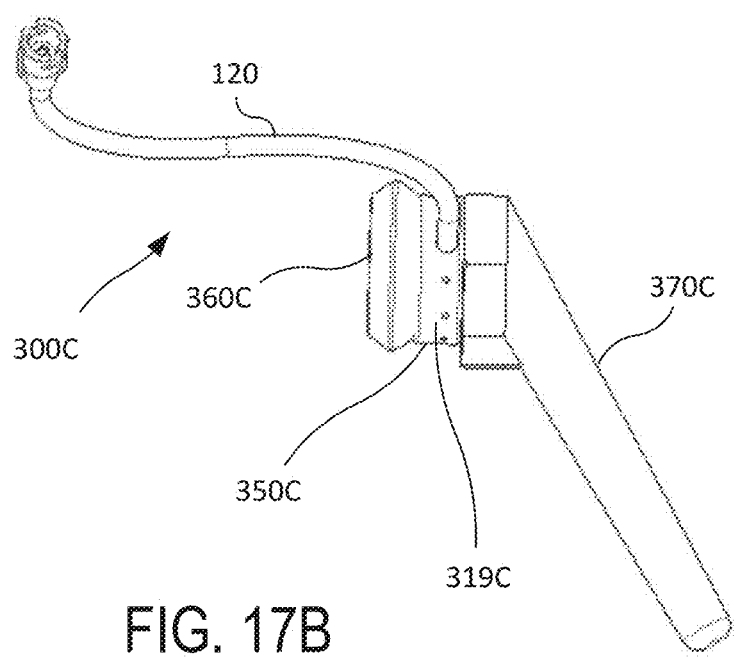

FIGS. 17A and 17B illustrate aspects of an exemplary reverse shoulder spacer system 300C. As depicted in the cross-section view of FIG. 17A, reverse shoulder spacer system 300C includes a reverse shoulder spacer 350C and a catheter 120. As shown in FIG. 17B, reverse shoulder spacer 350C includes a first surface configured for articulating engagement with a first implant (e.g. glenoid implant 360C), a second surface configured for fixed engagement with a second implant (e.g. humeral implant 370C), and an exposed surface 319C disposed between the first surface and the second surface. A reverse shoulder spacer 350C can include outlets through which treatment fluid may flow. For example, first surface can include outlets through which treatment fluid may flow toward a glenoid implant 360C, second surface can include outlets through which treatment fluid may flow toward a humeral implant 370C, and exposed surface 319C can include outlets through which treatment fluid may flow into a joint space between the glenoid implant 360C and the humeral implant 370C, for example to treat the nearby soft tissue.

Figure 18:
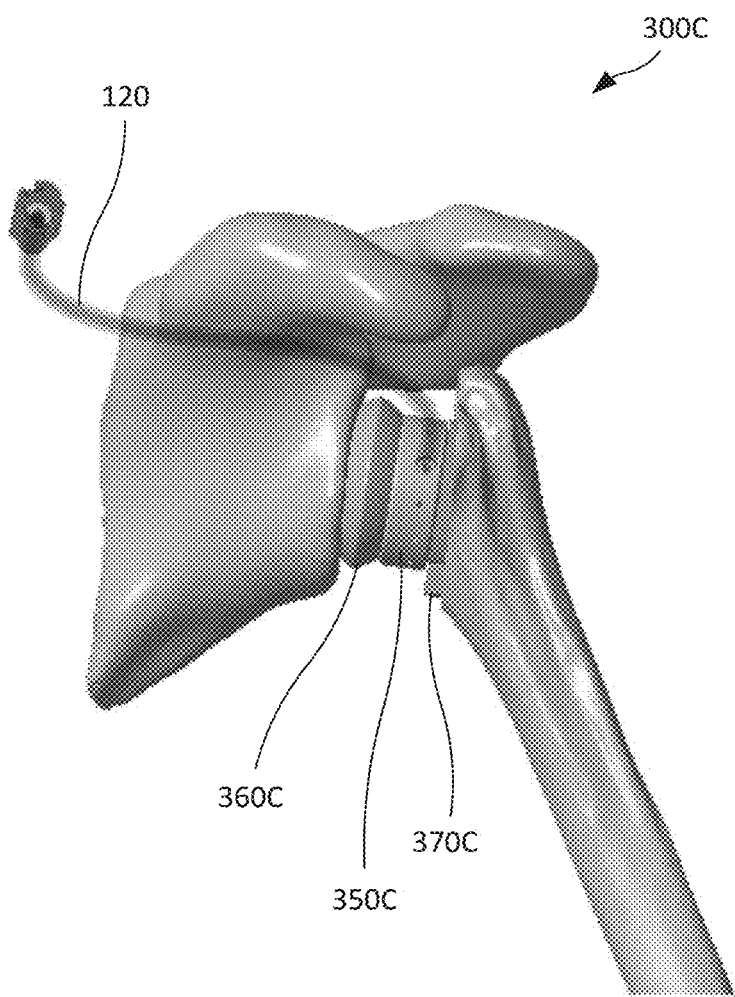
FIG. 18 depicts aspects of exemplary reverse shoulder spacer systems, according to embodiments of the present invention.

FIG. 18 depicts aspects of a reverse shoulder spacer system 300C, according to embodiments of the present invention. As shown here, the reverse shoulder spacer system 300C includes a reverse shoulder spacer 350C and a catheter 120. The reverse shoulder spacer 350C can engage a retained glenoid implant 360C which is attached with a glenoid bone. The reverse shoulder spacer 350C can also engage a retained humeral implant 370C which is attached with a humerus bone.

Methods of Treating Periprosthetic Joint Infection

Provided herein are methods of treating periprosthetic joint infection, the method comprising: providing one of: the hip spacer platform, the knee spacer platform, and the shoulder spacer platform; and supplying a medication to the pump to irrigate a location of the joint infection over a period of time. In some embodiments, the medication is supplied continuously over a period of time. In some embodiments, the medication is supplied intermittently over a period of time. In some embodiments, the medication is removed by applying negative pressure continuously to the site of joint infection. In some embodiments, the medication is removed by applying negative pressure intermittently over a period of time.

In some embodiments, the hip spacer platform comprises a hip spacer, a catheter in fluidic communication with the hip spacer, and a pump in fluidic communication with the hip spacer and the catheter. In some embodiments, the knee spacer platform comprises a knee spacer, a catheter in fluidic communication with the knee spacer, and a pump in fluidic communication with the knee spacer and the catheter. In some embodiments, the shoulder spacer platform comprises a shoulder spacer, a catheter in fluidic communication with the shoulder spacer, and a pump in fluidic communication with the shoulder spacer and the catheter.

In some embodiments, the medication comprises a broad spectrum of antibiotics. In some embodiments, the medication comprises tobramycin sulfate, vancomycin HCl, or both. In some embodiments, the medication comprises tobramycin sulfate for a first period of time and vancomycin HCl for a second period of time. In some embodiments, the period of time is about 1, 2, 3, 4, 5, 6, 7, 8, 9, 10, 11, 12, 13, 14 or more days.

Figure 19:
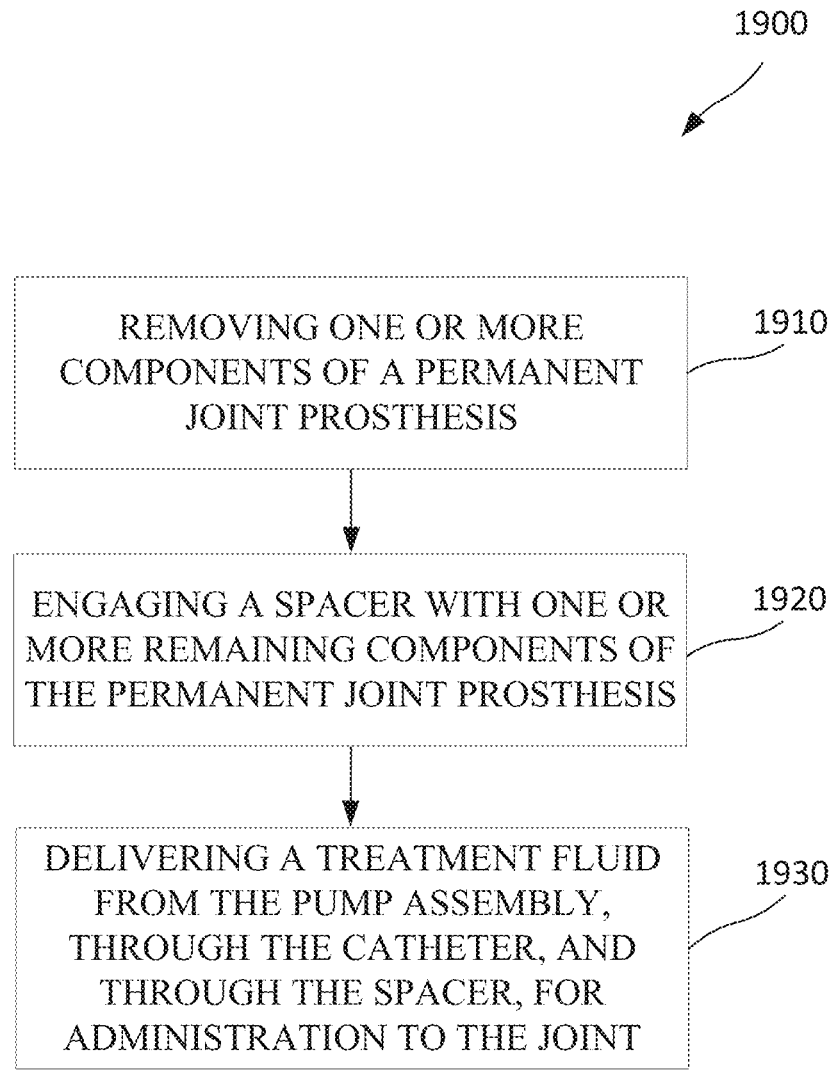
FIG. 19 illustrates aspects of exemplary treatment methods, according to embodiments of the present invention.

FIG. 19 depicts aspects of an exemplary method 1900 for treating a patient presenting with an acute periprosthetic joint infection of a joint, according to embodiments of the present invention. As shown here, the method 1900 can include removing one or more components of a permanent joint prosthesis, as depicted in step 1910. In some cases, a removal step may include removing one or more prosthetic components disposed between a first implant secured with a first bone of the joint and a second implant secured with a second bone of the joint. Methods may also include engaging a spacer of a spacer system with one or more remaining components of the permanent joint prosthesis, as depicted in step 1920. In some cases, the spacer system includes the spacer, a catheter, and a pump assembly. In some cases, the spacer and catheter are configured for detachable coupling. In some cases, the pump assembly is configured for coupling with the catheter. Methods may also include delivering a treatment fluid from the pump assembly, through the catheter, and through the spacer, for administration to the joint, as depicted in step 1930. In some cases, the delivery step 1930 can include delivering an antibiotic treatment fluid from the pump, through the catheter, into an inlet of the spacer. From the spacer, the fluid can flow out through a first plurality of outlets at a first surface of the spacer to the first implant, out through a second plurality of outlets at an exposed surface of the spacer and into a joint space between the first implant and the second implant, and out through a third plurality of outlets at a second surface of the spacer. The third plurality of outlets can be disposed within one or more fluted channels of the second surface so as to provide fluid flow between the spacer and the second implant. In some instances, the antibiotic treatment fluid is provided continuously or periodically to the patient over a treatment period of 7 days or more, and the catheter remains attached with the spacer throughout the treatment period Terms and Definitions Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Although embodiments of the present invention have been explained in relation to one or more preferred embodiments, it is to be understood that many other possible modifications and variations can be made without departing from the spirit and scope of the invention.

All features of the described systems and devices are applicable to the described methods *mutatis mutandis*, and vice versa.

Each reference provided herein in incorporated by reference in its entirety to the same extent as if each reference were individually incorporated by reference. Relatedly, all publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

While the above provides a full and complete disclosure of exemplary embodiments of the present invention, which have been has been described in some detail by way of illustration and example for purposes of clarity of understanding, one of skill in the art will appreciate that certain changes, various modifications, alternate constructions, and/or equivalents may be practiced or employed as desired, and within the scope of the appended claims. Accordingly, the above description and illustrations should not be construed as limiting the invention, which can be defined by the claims.

What is claimed is:

1. A spacer system for treating a patient presenting with a periprosthetic joint infection, the spacer system comprising:
   a spacer configured for placement between a first implant and a second implant of a permanent joint prosthesis; and
   a catheter, wherein the spacer and catheter are configured for detachable coupling;
   wherein the spacer comprises:
      a first surface having a convex shape configured for engagement with a corresponding concave shape of the first implant;
      a second surface having a concave shape configured for engagement with a corresponding convex shape of the second implant,
      an exposed surface disposed between the first surface and the second surface;
      a plurality of internal channels extending within the spacer, the plurality of internal channels configured in an array about a center axis of the spacer; and
      an inlet through the exposed surface that is configured to detachably couple to the catheter to receive a treatment fluid, the inlet coaxial with a first internal channel of the plurality of internal channels,
   wherein the exposed surface of the spacer comprises a first plurality of outlets in fluid communication with the inlet, such that, when the spacer is implanted in the patient, treatment fluid delivered into the inlet flows into the first internal channel of the plurality of internal channels toward the center axis before exiting out through the first plurality of outlets into a joint space between the first implant and the second implant.

2. A spacer system of claim 1, wherein the spacer system is a hip spacer system, the joint is a hip joint, the first implant is an acetabular cup, and the second implant is a femoral stem comprising a femoral head.

3. A spacer system of claim 1, wherein the second surface of the spacer comprises a plurality of fluted channels.

4. A spacer system of claim 3, wherein at least one of the fluted channels comprises a plurality of fluid outlets.

5. A spacer system of claim 3, wherein the plurality of fluted channels are arrayed about the center axis of the spacer.

6. A spacer system of claim 3, wherein, when the spacer is implanted, the plurality of fluted channels enables fluid flow under the spacer, between the spacer and the second implant.

7. A spacer system of claim 1, wherein the spacer is undersized relative to the first implant.

8. A spacer system of claim 1, wherein the spacer comprises a biocompatible polymer selected from the group consisting of low-density polyethylene (LDPE), high-density polyethylene (HDPE), polypropylene (PP), polyvinyl chloride (PVC) polystyrene (PS) nylon, polytetrafluoroethylene, a thermoplastic polyurethane (TPU), acetyl copolymer, silicone, polyether ether ketone (PEEK), a polyurethane, a biocompatible elastomer, and an ultrahigh molecular weight polyethylene (UHMWPE).

9. The spacer system of claim 1, wherein the first surface comprises a second plurality of outlets in fluid communication with the inlet and the plurality of internal channels, such that, when the spacer is implanted, treatment fluid delivered into the inlet flows out through the first plurality of outlets into the joint space and out through the second plurality of outlets to the first implant.

10. The spacer system of claim 9, wherein each internal channel of the plurality of internal channels extends within the spacer and terminates at a respective outlet of either the first plurality of outlets through the exposed surface or the second plurality of outlets through the first surface.

11. The spacer system of claim 1, wherein the first surface is configured for articulating engagement with the first implant.

12. The spacer system of claim 11, wherein the second surface of the spacer is configured for articulating engagement with the second implant.

13. The spacer system of claim 1, wherein the spacer is adapted for temporary placement between said first implant and said second implant of said permanent joint prosthesis.

14. A spacer platform comprising the spacer system of claim 1 and, further comprising a pump assembly configured for coupling to the catheter.

* * * * *